(12) United States Patent
Xiang et al.

(10) Patent No.: US 11,385,219 B2
(45) Date of Patent: Jul. 12, 2022

(54) HANDHELD DIAGNOSTIC TEST DEVICE AND METHOD FOR USE WITH AN ELECTRONIC DEVICE AND A TEST CARTRIDGE IN A RAPID DIAGNOSTIC TEST

(71) Applicant: Fio Corporation, Toronto (CA)

(72) Inventors: Qing Xiang, Toronto (CA); Jill Lindsey Osborne, Toronto (CA); Ryan Davey, Toronto (CA); Francois Dupoteau, Toronto (CA)

(73) Assignee: FIO Corporation, Toronto (CA)

(*) Notice: Subject to any disclaimer, the term of this patent is extended or adjusted under 35 U.S.C. 154(b) by 1118 days.

(21) Appl. No.: 15/706,258

(22) Filed: Sep. 15, 2017

(65) Prior Publication Data

US 2018/0004910 A1   Jan. 4, 2018

Related U.S. Application Data

(62) Division of application No. 13/144,438, filed as application No. PCT/CA2010/000033 on Jan. 13, 2010, now Pat. No. 9,805,165.

(60) Provisional application No. 61/144,283, filed on Jan. 13, 2009.

(51) Int. Cl.
| | | |
|---|---|---|
| *G01N 33/487* | (2006.01) | |
| *G16H 40/63* | (2018.01) | |
| *G16H 40/67* | (2018.01) | |
| *G01N 21/78* | (2006.01) | |
| *G01N 21/84* | (2006.01) | |
| *G01N 21/77* | (2006.01) | |

(52) U.S. Cl.
CPC ....... *G01N 33/48792* (2013.01); *G16H 40/63* (2018.01); *G16H 40/67* (2018.01); *G01N 21/78* (2013.01); *G01N 21/8483* (2013.01); *G01N 2021/7786* (2013.01)

(58) Field of Classification Search
CPC ... G01N 33/48792; G16H 40/67; G16H 40/63
USPC .......................................................... 702/19
See application file for complete search history.

(56) References Cited

U.S. PATENT DOCUMENTS

| | | |
|---|---|---|
| 5,244,630 A | 9/1993 | Khalil et al. |
| 5,662,824 A | 9/1997 | Sang et al. |
| 5,714,390 A | 2/1998 | Hallowitz et al. |
| 5,786,219 A | 7/1998 | Zhang et al. |
| 5,817,458 A | 10/1998 | King et al. |
| 5,837,442 A | 11/1998 | Tsang |
| 6,011,252 A | 1/2000 | Jensen |
| 6,022,500 A | 2/2000 | John et al. |
| 6,066,243 A | 5/2000 | Anderson et al. |
| 6,100,541 A | 8/2000 | Nagle et al. |
| 6,103,379 A | 8/2000 | Margel et al. |
| 6,114,038 A | 9/2000 | Castro et al. |
| 6,119,953 A | 9/2000 | Ganan-Calvo et al. |
| 6,172,193 B1 | 1/2001 | Primi et al. |
| 6,174,469 B1 | 1/2001 | Ganan-Calvo |
| 6,261,779 B1 | 6/2001 | Barbera-Guillem et al. |
| 6,267,722 B1 | 8/2001 | Anderson et al. |
| 6,274,323 B1 | 10/2001 | Bruchez et al. |
| 6,309,701 B1 | 10/2001 | Barbera-Guillem |
| 6,316,781 B1 | 11/2001 | Nagle et al. |
| 6,319,607 B1 | 11/2001 | Barbera-Guillem et al. |
| 6,333,110 B1 | 12/2001 | Barbera-Guillem |
| 6,340,588 B1 | 1/2002 | Nova et al. |
| 6,353,475 B1 | 3/2002 | Jensen et al. |
| 6,357,670 B2 | 3/2002 | Ganan-Calvo |
| 6,394,952 B1 | 5/2002 | Anderson et al. |
| 6,399,952 B1 | 6/2002 | Maher et al. |
| 6,409,900 B1 | 6/2002 | Parce et al. |
| 6,413,401 B1 | 7/2002 | Chow et al. |
| 6,430,512 B1 | 8/2002 | Gallagher |
| 6,468,808 B1 | 10/2002 | Nie et al. |
| 6,494,830 B1 | 12/2002 | Wessel |
| 6,498,353 B2 | 12/2002 | Nagle et al. |

(Continued)

FOREIGN PATENT DOCUMENTS

| | | |
|---|---|---|
| CA | 2061574 | 8/1992 |
| CA | 2021587 | 4/2003 |

(Continued)

OTHER PUBLICATIONS

Alivisatos, A.P., Perspectives on the Physical Chemistry of Semi¬conductor Nanocrystals, Journal of Physical Chemistry, 1996, pp. 13226-13239, vol. 100, No. 31, American Chemical Society, USA.

Bakalova, Rurniana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.

Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.

(Continued)

*Primary Examiner* — Jerry Lin
(74) *Attorney, Agent, or Firm* — SmithAmundsen LLC

(57) ABSTRACT

A handheld diagnostic test device includes a port to removably receive a test cartridge, an element connected with an electronic device, and sensors for detection of test data from a biological or environment sample after reaction with reagents onboard the cartridge. The test device also includes memory storing algorithms for upload to the electronic device to enable a processor thereof: to await elapse of a pre-determined time following reaction of the sample with the reagents; to thereafter instruct the sensors to detect the test data; to generate presentation data based on the test data; and to present the presentation data from a presentation element of the electronic device to a user. A related method includes a connecting step, an uploading step, a presentation step, a cartridge inserting step, a waiting step, a sensing step, and an electronic device processing step.

24 Claims, 11 Drawing Sheets

(56) References Cited

U.S. PATENT DOCUMENTS

| | | |
|---|---|---|
| 6,504,607 B2 | 1/2003 | Jensen et al. |
| 6,506,609 B1 | 1/2003 | Wada et al. |
| 6,514,399 B1 | 2/2003 | Parce et al. |
| 6,524,793 B1 | 2/2003 | Chandler et al. |
| 6,528,165 B2 | 3/2003 | Chandler |
| 6,544,732 B1 | 4/2003 | Chee et al. |
| 6,548,171 B1 | 4/2003 | Barbera-Guillem et al. |
| 6,548,264 B1 | 4/2003 | Tan et al. |
| 6,554,202 B2 | 4/2003 | Ganan-Calvo |
| 6,576,155 B1 | 6/2003 | Barbera-Guillem |
| 6,592,821 B1 | 7/2003 | Wada et al. |
| 6,592,822 B1 | 7/2003 | Chandler |
| 6,630,307 B2 | 10/2003 | Bruchez et al. |
| 6,632,655 B1 | 10/2003 | Mehta et al. |
| 6,649,138 B2 | 11/2003 | Adams et al. |
| 6,673,662 B2 | 1/2004 | Singh |
| 6,680,211 B2 | 1/2004 | Barbera-Guillem et al. |
| 6,681,821 B1 | 1/2004 | Cirone et al. |
| 6,699,188 B2 | 3/2004 | Wessel |
| 6,699,723 B1 | 3/2004 | Weiss et al. |
| 6,720,411 B2 | 4/2004 | Mirkin et al. |
| 6,734,420 B2 | 5/2004 | Empedodes et al. |
| 6,740,491 B2 | 5/2004 | Mirkin et al. |
| 6,752,966 B1 | 6/2004 | Chazan |
| 6,759,235 B2 | 7/2004 | Empedodes et al. |
| 6,767,706 B2 | 7/2004 | Quake et al. |
| 6,772,070 B2 | 8/2004 | Gilmanshin et al. |
| 6,773,812 B2 | 8/2004 | Chandler et al. |
| 6,778,724 B2 | 8/2004 | Wang et al. |
| 6,787,088 B2 | 11/2004 | Parce et al. |
| 6,835,326 B2 | 12/2004 | Barbera-Guillem |
| 6,867,051 B1 | 3/2005 | Anderson et al. |
| 6,872,249 B2 | 3/2005 | Peng et al. |
| 6,881,537 B1 | 4/2005 | Goudsmit et al. |
| 6,890,764 B2 | 5/2005 | Chee et al. |
| 6,905,885 B2 | 6/2005 | Colsten et al. |
| 6,936,476 B1 | 8/2005 | Anderson et al. |
| 6,966,880 B2 | 11/2005 | Boecker et al. |
| 6,978,212 B1 | 12/2005 | Sunshine |
| 6,986,837 B2 | 1/2006 | Chow et al. |
| 7,037,729 B2 | 5/2006 | Nie et al. |
| 7,041,362 B2 | 5/2006 | Barbera-Guillem |
| 7,069,191 B1 | 6/2006 | Moore |
| 7,077,328 B2 | 7/2006 | Kirchnaswamy et al. |
| 7,079,241 B2 | 7/2006 | Empedodes et al. |
| 7,041,468 B2 | 9/2006 | Drucker et al. |
| 7,166,475 B2 | 1/2007 | Colyer et al. |
| 7,171,983 B2 | 2/2007 | Chien et al. |
| 7,192,785 B2 | 3/2007 | Nie et al. |
| 7,243,670 B2 | 7/2007 | Witt et al. |
| 7,252,928 B1 | 8/2007 | Hafeman et al. |
| 7,267,799 B1 | 9/2007 | Borich et al. |
| 7,270,970 B2 | 9/2007 | Anderson et al. |
| 2001/0027918 A1 | 10/2001 | Parce et al. |
| 2001/0028055 A1 | 10/2001 | Fafard et al. |
| 2001/0046602 A1 | 11/2001 | Chandler et al. |
| 2001/0055764 A1 | 12/2001 | Empedodes et al. |
| 2002/0009728 A1 | 1/2002 | Bittner et al. |
| 2002/0022273 A1 | 2/2002 | Empedodes et al. |
| 2002/0031783 A1 | 3/2002 | Empedodes et al. |
| 2002/0037499 A1 | 3/2002 | Quake et al. |
| 2002/0045045 A1 | 4/2002 | Adams et al. |
| 2002/0048425 A1 | 4/2002 | McBride et al. |
| 2002/0051971 A1 | 5/2002 | Stuelpnagel et al. |
| 2002/0059030 A1 | 5/2002 | Otworth et al. |
| 2002/0066401 A1 | 6/2002 | Peng et al. |
| 2002/0118355 A1 | 8/2002 | Worthington et al. |
| 2002/0144644 A1 | 10/2002 | Zehnder et al. |
| 2002/0164271 A1 | 11/2002 | Ho |
| 2002/0182609 A1 | 12/2002 | Arcot |
| 2003/0003441 A1 | 1/2003 | Colston et al. |
| 2003/0017264 A1 | 1/2003 | Treadway et al. |
| 2003/0026740 A1 | 2/2003 | Staats |
| 2003/0050537 A1 | 3/2003 | Wessel |
| 2003/0073086 A1 | 4/2003 | Guire et al. |
| 2003/0099940 A1 | 5/2003 | Empedodes et al. |
| 2003/0132538 A1 | 7/2003 | Chandler |
| 2003/0148530 A1 | 8/2003 | Lauks |
| 2003/0148544 A1 | 8/2003 | Nie et al. |
| 2003/0157327 A1 | 8/2003 | Barbera-Guillem et al. |
| 2003/0165951 A1 | 9/2003 | Bruchez, Jr. et al. |
| 2003/0170613 A1 | 9/2003 | Straus et al. |
| 2003/0172343 A1 | 9/2003 | Guyon et al. |
| 2003/0175773 A1 | 9/2003 | Chee et al. |
| 2003/0176183 A1 | 9/2003 | Drucker et al. |
| 2003/0177038 A1 | 9/2003 | Rao |
| 2003/0177941 A1 | 9/2003 | Barbera-Guillem |
| 2003/0190628 A1 | 10/2003 | Nakao et al. |
| 2003/0194350 A1 | 10/2003 | Stamatelos et al. |
| 2004/0009341 A1 | 1/2004 | Naasani |
| 2004/0067485 A1 | 4/2004 | Mayes et al. |
| 2004/0072428 A1 | 4/2004 | Sato et al. |
| 2004/0096363 A1 | 5/2004 | Porter |
| 2004/0101621 A1 | 5/2004 | Adams et al. |
| 2004/0106218 A1 | 6/2004 | Wang et al. |
| 2004/0118684 A1 | 6/2004 | Wainright et al. |
| 2004/0147031 A1 | 7/2004 | Nakao |
| 2004/0176704 A1 | 9/2004 | Stevens et al. |
| 2004/0203170 A1 | 10/2004 | Barbera-Guillem |
| 2004/0204633 A1 | 10/2004 | Rentea et al. |
| 2004/0229261 A1 | 11/2004 | Young |
| 2004/0241424 A1 | 12/2004 | Barbera-Guillem |
| 2004/0241752 A1 | 12/2004 | Anderson et al. |
| 2004/0247861 A1 | 12/2004 | Naasani |
| 2004/0248167 A1 | 12/2004 | Quake et al. |
| 2004/0266022 A1 | 12/2004 | Sundararajan et al. |
| 2004/0267568 A1 | 12/2004 | Chandler et al. |
| 2005/0004346 A1 | 1/2005 | Dziegiel et al. |
| 2005/0009002 A1 | 1/2005 | Chen et al. |
| 2005/0011764 A1 | 1/2005 | Berndt et al. |
| 2005/0014134 A1 | 1/2005 | West et al. |
| 2005/0032047 A1 | 2/2005 | Simmonds et al. |
| 2005/0043894 A1 | 2/2005 | Fernandez et al. |
| 2005/0059030 A1 | 3/2005 | Bao et al. |
| 2005/0071199 A1 | 3/2005 | Riff |
| 2005/0106257 A1 | 5/2005 | Albayrak |
| 2005/0112277 A1 | 5/2005 | Banerjee et al. |
| 2005/0120946 A1 | 6/2005 | Hines et al. |
| 2005/0128479 A1 | 6/2005 | Gilbert et al. |
| 2005/0164264 A1 | 7/2005 | Shipwash |
| 2005/0201898 A1 | 9/2005 | Borich et al. |
| 2005/0214536 A1 | 9/2005 | Schrier et al. |
| 2005/0221296 A1 | 10/2005 | Simmonds et al. |
| 2005/0227370 A1 | 10/2005 | Ramel et al. |
| 2005/0239118 A1 | 10/2005 | Goudsmit et al. |
| 2005/0239156 A1 | 10/2005 | Drucker et al. |
| 2005/0277164 A1 | 12/2005 | Drucker et al. |
| 2006/0008921 A1 | 1/2006 | Daniels et al. |
| 2006/0008923 A1 | 1/2006 | Anderson et al. |
| 2006/0012784 A1 | 1/2006 | Ulmer |
| 2006/0014040 A1 | 1/2006 | Peng et al. |
| 2006/0014302 A1 | 1/2006 | Martinez et al. |
| 2006/0019098 A1 | 1/2006 | Chan et al. |
| 2006/0029267 A1 | 2/2006 | Frost et al. |
| 2006/0046330 A1 | 3/2006 | Chen et al. |
| 2006/0063160 A1 | 3/2006 | West et al. |
| 2006/0068203 A1 | 3/2006 | Ying et al. |
| 2006/0078490 A1 | 4/2006 | Shih et al. |
| 2006/0105335 A1 | 5/2006 | Daehne et al. |
| 2006/0152372 A1 | 7/2006 | Stout |
| 2006/0169800 A1 | 8/2006 | Rosell et al. |
| 2006/0173715 A1 | 8/2006 | Wang |
| 2006/0194030 A1 | 8/2006 | Barbera-Guillem |
| 2007/0020779 A1 | 1/2007 | Stavis et al. |
| 2007/0031283 A1 | 2/2007 | Davis et al. |
| 2007/0081920 A1 | 4/2007 | Murphy et al. |
| 2009/0164134 A1 | 6/2009 | Drucker et al. |
| 2009/0216105 A1 | 8/2009 | Drucker et al. |

FOREIGN PATENT DOCUMENTS

| | | |
|---|---|---|
| CA | 2518352 | 3/2005 |
| EP | 1315099 | 5/2003 |
| JP | 2002-271 | 1/2002 |

(56) References Cited

FOREIGN PATENT DOCUMENTS

| JP | 2005-508493 | 3/2005 |
|---|---|---|
| WO | WO 99/19000 | 4/1999 |
| WO | WO 99/36564 | 7/1999 |
| WO | WO 99/64840 | 12/1999 |
| WO | WO 99/66318 | 12/1999 |
| WO | WO 00/13580 | 3/2000 |
| WO | WO 00/28598 | 5/2000 |
| WO | WO 00/70080 | 11/2000 |
| WO | WO 01/20533 | 3/2001 |
| WO | WO 01/89585 | 11/2001 |
| WO | WO 01/93754 | 12/2001 |
| WO | WO 02/04484 | 1/2002 |
| WO | WO 03/003015 | 1/2003 |
| WO | WO 2004/008550 | 1/2004 |
| WO | WO 2004/040319 | 5/2004 |
| WO | WO 2005/023923 | 3/2005 |
| WO | WO 2005/031802 | 4/2005 |
| WO | WO 2005/052996 | 6/2005 |
| WO | WO 2005/053649 | 6/2005 |
| WO | WO 2005/061095 | 7/2005 |
| WO | WO 2006/033732 | 3/2006 |
| WO | WO 2006/045004 | 4/2006 |
| WO | WO 2006/072306 | 7/2006 |
| WO | WO 2006/132953 | 12/2006 |
| WO | WO 2007/011622 | 1/2007 |
| WO | WO 2008/089155 | 7/2008 |
| WO | WO 2008/147382 | 12/2008 |
| WO | WO 2009/059404 | 5/2009 |

OTHER PUBLICATIONS

Branch, Mary Ann et al., A Subspace, Interior, and Conjugate Gradient Method for Large-Scale Bound-Constrained Minimization Problems, Siam J. Sci. Comput, Aug. 3, 1999, pp. 1-23, vol. 21, No. 1, Society for Industrial and Applied Mathematics.
Bruchez, Marcel Jr. et at., Semiconductor Nanocrystals as Fluores¬cent Biological Labels, Science, Sep. 25, 1998, pp. 2013-2015, vol. 281, American Association for the Advancement of Science, USA.
Burns, Mark A. et al., An Integrated Nanoliter DNA Analysis Device, Science, Oct. 16, 1998, pp. 484-487, vol. 282, No. 5388, American Association for the Advancement of Science, USA.
Chabinyc, Michael L. et al., An Integrated Fluorescence Detection System in Poly (dimethylsiloxane) for Microfluidic Applications, Analytical Chemistry, Sep. 15, 2001, pp. 4494-4498, vol. 73, No. 18, American Chemical Society, USA.
Chan, Eugene Y. et al., DNA Mapping Using Microfluidic Stretch¬ing and Single-Molecule Detection of Fluorescent Site-Specific Tags, Genome Research, 2004, pp. 1137-1146, vol. 14, Cold Spring Harbour Laboratory Press, USA.
Chan, Warren C. W. et al., Luminescent quantum dots for multi¬plexed biological detection and imaging, Current Opinion in Bio¬technology, 2002, pp. 40-46, vol. 13, Elsevier Science Ltd.
Chan, Warren C. W. et al., Quantum Dot Bioconjugates for Ultrasensitive Nonisotopic Detection, Science, Sep. 25, 1998, pp. 2016-2018, vol. 281, American Association for the Advancement of Science, USA.
Chou, Hou-Pu et al., A microfabricated device for sizing and sorting DNA molecules, PNAS-Proceedings of the National Academy of Sciences of the United States of America, Jan. 1999, pp. 11-13, vol. 96, The National Academy of Sciences, USA.
Dabbousi, B.O. et al., (CdSe)ZnS Core-Shell Quantum Dots: Syn¬thesis and Characterization of a Size Series of Highly Luminescent Nanocrystallites, Journal of Physical Chemistry B, 1997, pp. 9463-9475, vol. 101, No. 46, American Chemical Society, USA.
Duffy, D.C. et al., Rapid Prototyping of Microfulidic Systems in Poly(dimethylsiloxane), Analytical Chemistry, Dec. 1, 1998, pp. 4974-4984, vol. 70, No. 23, American Chemical Society, USA.
Eisenstein, Michael, Technology Feature: Protein Arrays-Growing pains, Losing the Label, an Apt Solution? & (Almost) No Assembly Required, Nature, Dec. 14, 2006, pp. 959-962, vol. 444, Nature Publishing Group, USA.

Fournier-Bidoz, Sebastien et al., Facile and Rapid One-Step Mass Preparation of Quantum-Dot Barcodes, Angewandte Chemie Inter¬national Edition, 2008, pp. 5577-5581, vol. 47, No. 30, Wiley-VCH Verlag GmbH & Co. KGaA, Weinheim.
Fu, Anne Y et al., A microfabricated fluorescence-activated cell sorter, Nature Biotechnology, Nov. 1999, pp. 1109-1111, vol. 17, Nature America Inc., USA.
Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.
Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.
Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.
Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.
Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.
Gershon, Diane, Technology Feature: DNA Microarrays-More than than gene expression, It's a Small World, Microassays Move Downstream & on the Hardware Front, Nature, Oct. 20, 2005, pp. 1195-1198, vol. 437, Nature Publishing Group, USA.
Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.
Grumann, M. et al., Parallelization of Chip-Based Fluorescence Immuno-Assays with Quantum-Dot Labelled Beads, the 13th Inter¬national Conference on Solid-State Sensors, Actuators and Microsystems, Jun. 2005, pp. 1114-1117, IEEE.
Han, Mingyong et al., Quantum-dot-tagged microbeads for multi¬plexed optical coding of biomolecules, Nature Biotechnology, Jul. 2001, pp. 631-635, vol. 19, Nature Publishing Group, USA.
Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.
Kloepfer, Jeremiah A. et al., Photophysical Properties of Biologi¬cally Compatible CdSe Quantum Dot Structures, Journal of Physi¬cal Chemistry B, 2005, pp. 9996-10003, vol. 109, No. 20, American Chemical Society, USA.
Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.
Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.
Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.
Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.
Malamud, D. et al., Point Detection of Pathogens in Oral Samples, Adv Dent Res, Jun. 2005, pp. 12-16. vol. 18.
Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.
Mattoussi, H. et al., Luminescent Quantum Dot-Bioconjugates in Immunoassays, FRET, Biosensing, and Imaging Applications, JALA-

(56) References Cited

OTHER PUBLICATIONS

Journal of the Association for Laboratory Automation, Feb. 2004, pp. 28-32, vol. 9, No. 1, The Association for Laboratory Automation, USA.
Medintz, Igor L. et al., Quantum dot bioconjugates for imaging, labelling and sensing, Nature Materials, Jun. 2005, pp. 435-446, vol. 4, Nature Publishing Group, USA.
More, Jorge J. et al., Computing a Trust Region Step, SIAM J. Sci. Stat. Comput., Sep. 1983, pp. 553-572, vol. 4, No. 3, Society for Industrial and Applied Mathematics.
Murray, C.B. et al., Synthesis and Characterization of Nearly Monodisperse CdE (E = S, Se, Te) Semiconductor Nanocrystallites, Journal of the American Chemical Society, 1993, pp. 8706-8715, vol. 115, No. 19, American Chemical Society, USA.
Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.
Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.
Pregibon, Daniel C. et al., Multifunctional Encoded Particles for High-Throughput Biomolecule Analysis, Science, Mar. 9, 2007, pp. 1393-1396, vol. 315, American Association for the Advancement of Science, Usa [downloaded on Mar. 9, 2009 from http://www.sciencemag.org].
Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, vol. 78, No. 16, American Chemical Society, USA.
Service, Robert F., DNA Analysis: Microchip Arrays Put DNA on the Spot, Science, Oct. 16, 1998, pp. 396-399, vol. 282, No. 5388, American Association for the Advancement of Science, USA [downloaded on Mar. 20, 2008 from http://www.sciencemag.org/ cgi/content/full/282/5388/396].
Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.
Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.
Thomson, B. et al., Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.
Xu, Hongxia et al., Muliplexed SNP genotyping using the Qbead™ system: a quantum dot-encoded microsphere-based assay, Nucleic Acids Research, 2003, pp. 1-10, vol. 31, No. 8, Oxford University Press.
Xuan, Xiangchun et al., Focused electrophoretic motion and selected electrokinetic dispensing of particles of particles and cells in cross-microchannels, Electrophoresis, 2005, pp. 3552-3560, vol. 26, Wiley-VCH Verlag GmbH co. KGaA, Weinheim.
Yun, Kwang-Seok et al., A microfluidic chip for measurement of biomolecules using a microbead-based quantum dot fluorescence assay, Measurement Science and Technology, 2006, pp. 3178-3183, vol. 17, IOP Publishing Ltd, UK.
Zaytseva, Natalya V. et al., Development of a microfluidic biosensor module for pathogen detection, Lab on a Chip, Jul. 6, 2005, pp. 805-811, vol. 5, The Royal Society of Chemistry.
International Preliminary Report on Patentability Chapter II from PCT/CA2010/000033 dated May 9, 2011.
Written Opinion of the International Search Authority from PCT/CA2010/000033 dated Mar. 9, 2010.
International Search Report from PCT/CA2010/00003 3 dated Mar. 9, 2010.

HANDHELD DIAGNOSTIC TEST DEVICE AND METHOD FOR USE WITH AN ELECTRONIC DEVICE AND A TEST CARTRIDGE IN A RAPID DIAGNOSTIC TEST

CROSS REFERENCE TO RELATED APPLICATIONS

This is a divisional application of U.S. application Ser. No. 13/144,438 filed Jan. 13, 2012, which is a U.S. National Stage Application of International Application No. PCT/CA2010/000033 filed Jan. 13, 2010, which claims priority from U.S. Application No. 61/144,283 filed Jan. 13, 2009. The entireties of the above-listed applications are incorporated herein by reference.

FIELD OF THE INVENTION

The present invention relates generally to diagnostic test devices, and more particularly, to a handheld diagnostic test device and method for use with an electronic device and a test cartridge in a rapid diagnostic test.

BACKGROUND OF THE INVENTION

Previously, rudimentary rapid tests may have been available on the market. Tests of this nature may have afforded a testing of only relatively basic parameters, such as typically may not have required any interpretation and/or a data management process in order to validate the test. More sophisticated and/or accurate rapid point-of-care tests may not heretofore have been possible, apart from at the hospital and/or in a core laboratory. This shortcoming of the prior art may have been due, in part, to the complexity of these kinds of diagnostic tests. At the same time, most prior art tests (whether simple or complex) may heretofore have required medical interpretation by qualified personnel.

Previously, in addition, the recordal of data in a computer for analysis and/or compilation in an electronic medical record (EMR) or healthcare repository may only have occurred in environments where there was access to a laboratory information system (LIS) or a hospital information system (HIS). That is, heretofore, automated recordal of results related to patient identification may have been, at best, very difficult and, often, impossible with simple prior art tests (e.g., lateral flow strips).

Though the prior art may have included a few somewhat inexpensive test readers, the functionality heretofore afforded by such readers may generally have been somewhat limited. For example, some such readers may have required a separate computer to provide any quantitative test results whatsoever. The prior art may include: a Reader 100 device which may have been previously offered by MATEST Systemtechnik GmbH of Mossingen, Germany; and a device which may have been previously offered by Alverix, Inc. of San Jose, Calif.

It is an object of an aspect of one preferred embodiment according to the present invention to provide a handheld diagnostic test device and method for use with an electronic device and a test cartridge in a rapid diagnostic test.

It is an object of an aspect of one preferred embodiment according to the present invention to provide diagnostic test devices and/or methods which may preferably combine a diagnostic test device with a conventional computing or networking electronic device.

It is an object of an aspect of one preferred embodiment according to the present invention to provide diagnostic test devices and/or methods which may preferably combine a diagnostic test device with a cellular telephone or other electronic device.

It is an object of an aspect of one preferred embodiment according to the present invention to provide an integrated diagnostic reader and cellular telephone device and/or method.

It is an object of an aspect of one preferred embodiment according to the present invention to provide a diagnostic test device and/or method controllable by an electronic device.

It is an object of an aspect of one preferred embodiment according to the present invention to provide a diagnostic test device and/or method for use with an electronic device, with little or no modification of the electronic device hardware being required.

It is an object of an aspect of one preferred embodiment according to the present invention to provide a diagnostic test device and/or method for use with a networking electronic device, while allowing the networking electronic device to remain partially or fully functional as such.

It is an object of an aspect of one preferred embodiment according to the present invention to provide a diagnostic test device and/or method which uploads onto an electronic device one or more algorithms associated with a rapid diagnostic test for use by the electronic device.

It is an object of an aspect of one preferred embodiment according to the present invention to provide a diagnostic test device and/or method which, with upload of algorithms therefrom, enables a data input device and/or presentation element onboard an electronic device to be utilized in association with a rapid diagnostic test.

It is an object of an aspect of one preferred embodiment according to the present invention to provide a diagnostic test device and/or method which may be powered by the power supply of an electronic device.

It is an object of an aspect of one preferred embodiment according to the present invention to provide a diagnostic test device and/or method for use with an electronic device in rapidly performing quantitative and/or qualitative diagnostic tests.

It is an object of an aspect of one preferred embodiment according to the present invention to provide a diagnostic test device and/or method for use with an electronic device to enable assay time counting.

It is an object of an aspect of one preferred embodiment according to the present invention to provide a diagnostic test device and/or method for use with an electronic device to afford a location tracking capability, preferably a geo-localization and/or global location tracking capability.

It is an object of an aspect of one preferred embodiment according to the present invention to provide a diagnostic test device and/or method for use with an electronic device to enable secure management of patient data.

It is an object of an aspect of one preferred embodiment according to the present invention to provide a diagnostic test device and/or method for use with an electronic device in infectious disease surveillance, diagnosis and emergency medical response at the point of care.

It is an object of an aspect of one preferred embodiment according to the present invention to reduce the number of complex features or requirements (e.g., IT infrastructure, connectivity, and/or professional interpretation of result)

which may have been previously associated with substantially complete diagnostic test devices, systems and/or methods.

It is an object of an aspect of one preferred embodiment according to the present invention to provide substantially complete diagnostic test devices and/or methods which may preferably be used with few or no complex features or requirements, such as, for example, IT infrastructure, connectivity, and/or professional interpretation of result.

It is an object of an aspect of one preferred embodiment according to the present invention to provide diagnostic test devices and/or methods which afford a quality, level of result, and/or services which, heretofore, may only have been available in diagnostic tests performed in a core laboratory or hospital.

It is an object of an aspect of one preferred embodiment according to the present invention to provide diagnostic test devices, systems and/or methods which may preferably be used by a patient and/or customer with minimal technical or clinical knowledge concerning the device technology or the interpretation of the test results.

It is an object of one preferred embodiment according to the invention to provide a device and/or method for use in biological and/or medical applications.

It is an object of the present invention to obviate or mitigate one or more of the aforementioned mentioned disadvantages associated with the prior art, and/or to achieve one or more of the aforementioned objects of the invention.

SUMMARY OF THE INVENTION

According to the invention, there is disclosed a handheld diagnostic test device for use with a test cartridge containing one or more reagents to be reacted with a biological and/or environmental sample in a rapid diagnostic test. The test device is also for use an electronic device having an electronic device processor, an electronic device presentation element, and an electronic device connection element. The test device includes a test cartridge port to selectively receive the test cartridge in removable relation, a test device connection element connected with the electronic device connection element, and one or more sensors for operative detection of test data from the sample after reaction with the reagents. The test device also includes an onboard memory electronically storing one or more algorithms for electronic transmission to the electronic device, via the test device connection element and the electronic device connection element, such as to enable the electronic device processor to: (i) await elapse of a pre-determined time following reaction of the sample with the reagents; (ii) instruct at least one of the sensors to detect the test data after elapse of the pre-determined time following reaction of the sample with the reagents; (iii) generate presentation data based at least in part on the test data; and (iv) present the presentation data from the electronic device presentation element to a user.

According to an aspect of one preferred embodiment of the invention, the test device connection element may preferably, but need not necessarily, be connected with the electronic device connection element in selectively disconnectable relation.

According to an aspect of one preferred embodiment of the invention, the electronic transmission of the algorithms from the onboard memory may preferably, but need not necessarily, be such as to enable the electronic device processor to generate time counting data during elapse of the pre-determined time. The time counting data may preferably, but need not necessarily, form at least part of the presentation data for presentation to the user.

According to an aspect of one preferred embodiment of the invention, the test data may preferably, but need not necessarily, be electronically transmitted from the sensors to the electronic device via the test device connection element and/or the electronic device connection element. The electronic transmission of the algorithms from the onboard memory may preferably, but need not necessarily, be such as to enable the electronic device processor to generate test results based on the test data. The test results may preferably, but need not necessarily, form at least part of the presentation data for presentation to the user.

According to an aspect of one preferred embodiment of the invention, the test device may preferably, but need not necessarily, also include a test device processor electronically receiving the test data from the sensors and/or generating test results based on the test data. The test results may preferably, but need not necessarily, be electronically transmitted from the test device connection element to the electronic device via the electronic device connection element. The electronic device processor may preferably, but need not necessarily, generate the presentation data based at least in part on the test results.

According to an aspect of one preferred embodiment of the invention, the electronic transmission of the algorithms from the onboard memory may preferably, but need not necessarily, be such as to enable the electronic device processor to generate treatment and/or follow-up suggestion data for presentation to the user as at least part of the presentation data. The treatment and/or follow-up suggestion data may preferably, but need not necessarily, be based at least in part on the test results.

According to an aspect of one preferred embodiment of the invention, the test device may preferably, but need not necessarily, be for integral use with the electronic device. The test device connection element may preferably, but need not necessarily, be physically connected with the electronic device connection element in mating relation.

According to an aspect of one preferred embodiment of the invention, the test device may preferably, but need not necessarily, be adapted for use with a test cartridge identification element onboard the test cartridge. At least one of the sensors may preferably, but need not necessarily, operatively detect test cartridge identification data from the test cartridge identification element. The test cartridge identification data may preferably, but need not necessarily, be such as to enable identification of the rapid diagnostic test, the reagents, and/or associated quality assurance information.

According to an aspect of one preferred embodiment of the invention, the test device may preferably, but need not necessarily, be adapted for use with a bar code element and/or a radio-frequency identification (RFID) element as the test cartridge identification element.

According to an aspect of one preferred embodiment of the invention, the electronic transmission of the algorithms from the onboard memory may preferably, but need not necessarily, be such as to enable the electronic device processor to instruct the test device to initiate a self-check, calibration and/or maintenance routine.

According to an aspect of one preferred embodiment of the invention, the test device may preferably, but need not necessarily, be adapted for use with a data input device onboard the electronic device. The electronic transmission of the algorithms from the onboard memory may preferably, but need not necessarily, be such as to enable the electronic device processor to: (i) electronically receive, preferably via the data input device, user and/or patient identification data associated with the rapid diagnostic test; and/or (ii) generate the presentation data based in part on the user and/or patient identification data for presentation to the user.

According to an aspect of one preferred embodiment of the invention, the test device may preferably, but need not necessarily, be adapted for use with a keypad as the data input device.

According to an aspect of one preferred embodiment of the invention, the test device may preferably, but need not necessarily, be adapted for use with a networking electronic device as the electronic device. The electronic transmission of the algorithms from the onboard memory may preferably, but need not necessarily, be such as to enable: (i) the electronic device processor to encrypt the patient identification data as encrypted data; and/or (ii) the networking electronic device to transmit, preferably without the patient identification data, at least a portion of the presentation data, the test data, and/or the encrypted data for recordal in one or more remote and/or distributed databases.

According to an aspect of one preferred embodiment of the invention, the transmission of the presentation data, the test data, and/or the encrypted data by the networking electronic device and/or the encryption of the patient identification data may preferably, but need not necessarily, be fully compliant with all applicable interface standards for exchanging and/or transferring health data.

According to an aspect of one preferred embodiment of the invention, the test device may preferably, but need not necessarily, be adapted for use with a networking electronic device as the electronic device. The electronic transmission of the algorithms from the onboard memory may preferably, but need not necessarily, be such as to enable the networking electronic device to transmit at least a portion of the presentation data and/or the test data for recordal in one or more remote and/or distributed databases.

According to an aspect of one preferred embodiment of the invention, the test device may preferably, but need not necessarily, be adapted for use with a geo-localization element onboard the electronic device. The electronic transmission of the algorithms from the onboard memory may preferably, but need not necessarily, be such as to enable: (i) the electronic device processor to use the geo-localization element to obtain geo-localization data for the rapid diagnostic test; and/or (ii) the networking electronic device to transmit the geo-localization data for recordal in the remote and/or distributed databases.

According to an aspect of one preferred embodiment of the invention, the test device may preferably, but need not necessarily, also include a light source element illuminating the sample after elapse of the pre-determined time following reaction with the reagents. The aforesaid at least one of the sensors may preferably, but need not necessarily, include a photodiode element. The test data may preferably, but need not necessarily, include a test image.

According to an aspect of one preferred embodiment of the invention, the photodiode element may preferably, but need not necessarily, include a charge coupled device (CCD) element.

According to an aspect of one preferred embodiment of the invention, the light source element may preferably, but need not necessarily, include a laser, a light emitting diode (LED), an optical fiber light source element, a tungsten lamp, a mercury lamp, and/or a xenon lamp.

According to an aspect of one preferred embodiment of the invention, the test device may preferably, but need not necessarily, be adapted for use with an electronic device memory onboard the electronic device. The electronic transmission of the algorithms from the onboard memory may preferably, but need not necessarily, be such as to enable the electronic device processor to store the presentation data and/or the test data in the electronic device memory.

According to an aspect of one preferred embodiment of the invention, the test device may preferably, but need not necessarily, be adapted for use with a display element as the presentation element. The electronic transmission of the algorithms from the onboard memory may preferably, but need not necessarily, be such as to enable the electronic device processor to generate the presentation data for presentation from the display element, preferably in the form of one or more visually presentable (a) textual data, (b) graphical data, and/or (c) colored indicator light data.

According to an aspect of one preferred embodiment of the invention, the test device may preferably, but need not necessarily, also include a test device battery to power the test device.

According to an aspect of one preferred embodiment of the invention, the test device may preferably, but need not necessarily, be adapted for use with an electronic device battery onboard the electronic device. The test connection element of the test device may preferably, but need not necessarily, receive power, preferably via the electronic connection element, from the electronic device battery.

According to an aspect of one preferred embodiment of the invention, the test device may preferably, but need not necessarily, be adapted for use with one or more of following as the electronic device: (a) a cellular telephone; (b) a mobile communications device; (c) a personal digital assistant; (d) a desktop computer; (e) a laptop computer; (f) a navigation device; (g) a digital audio player; (h) a camera; (i) a gaming device; (j) a television; and/or (k) a radio.

According to the invention, there is also disclosed a method of testing a biological and/or environmental sample for use with one or more reagents carried by a test cartridge in a rapid diagnostic test. The method is also for use with an electronic device and a handheld diagnostic test device. The method includes the following steps: (a) a connecting step of connecting a test device connection element of the test device with an electronic device connection element of the electronic device; (b) an uploading step, after the connecting step, of electronic transmitting one or more algorithms electronically stored in an onboard memory of the test device to the electronic device, via the test device connection element and the electronic device connection element; (c) a presentation step, after the uploading step, of using the algorithms to enable an electronic device processor onboard the electronic device to present presentation data from an electronic device presentation element onboard the electronic device to a user; (d) a cartridge inserting step, after the connecting step and the uploading step, of inserting the test cartridge into a port in the test device, with the test cartridge serving as a substrate for reaction of the sample with the reagents; (e) a waiting step, preferably but not necessarily after the cartridge inserting step, of using the algorithms to enable the electronic device processor to await elapse of a pre-determined time following reaction of the sample with the reagents; (f) a sensing step, after the waiting step and the cartridge inserting step, of using the algorithms to enable the electronic device processor to instruct one or more sensors to detect test data from the sample; and (g) an electronic device processing step, after the sensing step, of using the algorithms to enable the electronic device processor to generate, based on the test data, at least a portion of the presentation data presented to the user.

According to an aspect of one preferred embodiment of the invention, preferably in the connecting step, the test device connection element may preferably, but need not necessarily, be connected with the electronic device connection element in selectively disconnectable relation.

According to an aspect of one preferred embodiment of the invention, preferably during the waiting step, the algorithms may preferably, but need not necessarily, enable the electronic device processor to generate time counting data. The time counting data may preferably, but need not necessarily, form at least a portion of the presentation data presented to the user.

According to an aspect of one preferred embodiment of the invention, preferably before the electronic device processing step, the test data may preferably, but need not necessarily, be electronically transmitted from the sensors to the electronic device via the test device connection element and/or the electronic device connection element. Preferably in the electronic device processing step, the algorithms may preferably, but need not necessarily, enable the electronic device processor to generate test results based on the test data. The test results may preferably, but need not necessarily, form at least part of the presentation data for presentation to the user.

According to an aspect of one preferred embodiment of the invention, the method may preferably, but need not necessarily, also include a test device processing step, preferably before the electronic device processing step, of using a test device processor onboard the test device to electronically receive the test data from the sensors and/or to generate test results based on the test data. Preferably before the electronic device processing step, the test results may preferably, but need not necessarily, be electronically transmitted from the test device connection element to the electronic device via the electronic device connection element. Preferably in the electronic device processing step, the algorithms may preferably, but need not necessarily, enable the electronic device processor to generate the presentation data based at least in part on the test results.

According to an aspect of one preferred embodiment of the invention, preferably in the electronic device processing step, the algorithms may preferably, but need not necessarily, enable the electronic device processor to generate treatment and/or follow-up suggestion data for presentation to the user as at least part of the presentation data. The treatment and/or follow-up suggestion data may preferably, but need not necessarily, be based at least in part on the test results.

According to an aspect of one preferred embodiment of the invention, preferably in the connecting step, the test device connection element may preferably, but need not necessarily, be physically connected with the electronic device connection element in mating relation.

According to an aspect of one preferred embodiment of the invention, the method may preferably, but need not necessarily, also include a cartridge identification step, preferably before the electronic device processing step, of using at least one of the sensors to operatively detect test cartridge identification data from a test cartridge identification element onboard the test cartridge, and/or using the test cartridge identification data to identify the rapid diagnostic test, the reagents, and/or associated quality assurance information.

According to an aspect of one preferred embodiment of the invention, preferably in the cartridge identification step, a bar code element and/or a radio-frequency identification (RFID) element may preferably, but need not necessarily, be used as the test cartridge identification element.

According to an aspect of one preferred embodiment of the invention, the method may preferably, but need not necessarily, also include a maintenance step, preferably after the uploading step, of using the algorithms to enable the electronic device processor to instruct the test device to initiate a self-check, calibration and/or maintenance routine.

According to an aspect of one preferred embodiment of the invention, the method may preferably, but need not necessarily, also include a data input step, preferably after the uploading step, of using the algorithms to enable the electronic device processor to electronically receive, preferably via a data input device onboard the electronic device, user and/or patient identification data associated with the rapid diagnostic test. Preferably in the electronic device processing step, the algorithms may preferably, but need not necessarily, enable the electronic device processor to generate the presentation data based in part on the user and/or patient identification data for presentation to the user.

According to an aspect of one preferred embodiment of the invention, preferably in the data input step, a keypad may preferably, but need not necessarily, be used as the data input device.

According to an aspect of one preferred embodiment of the invention, preferably in the connecting step, the electronic device may preferably, but need not necessarily, be a networking electronic device. The method may preferably, but need not necessarily, also include an encryption step, preferably after the data input step, of using the algorithms to enable the electronic device processor to encrypt the patient identification data as encrypted data. The method may preferably, but need not necessarily, also include a networking step, preferably after the electronic device processing step and/or the encryption step, of using the algorithms to enable the electronic device to transmit, preferably without the patient identification data, at least a portion of the presentation data, the test data, and/or the encrypted data for recordal in one or more remote and/or distributed databases.

According to an aspect of one preferred embodiment of the invention, preferably in the networking step, the transmission of the presentation data, the test data, and/or the encrypted data by the electronic device and/or the encryption of the patient identification data may preferably, but need not necessarily, be fully compliant with all applicable interface standards for exchanging and/or transferring health data.

According to an aspect of one preferred embodiment of the invention, preferably in the connecting step, the electronic device may preferably, but need not necessarily, be a networking electronic device. The method may preferably, but need not necessarily, also include a networking step, preferably after the electronic device processing step, of using the algorithms to enable the electronic device to transmit at least a portion of the presentation data and/or the test data for recordal in one or more remote and/or distributed databases.

According to an aspect of one preferred embodiment of the invention, the method may preferably, but need not necessarily, also include a geo-localization step, preferably before the networking step, of using the algorithms to enable the electronic device processor to use a geo-localization element onboard the electronic device to obtain geo-localization data for the rapid diagnostic test. Preferably in the networking step, the algorithms may preferably, but need not necessarily, enable the networking electronic device to transmit the geo-localization data for recordal in the remote and/or distributed databases.

According to an aspect of one preferred embodiment of the invention, preferably in the sensing step, a light source element onboard the test device may preferably, but need not necessarily, illuminate the sample. At least one of the sensors may preferably, but need not necessarily, include a photodiode element. The test data may preferably, but need not necessarily, include a test image.

According to an aspect of one preferred embodiment of the invention, preferably in the sensing step, the photodiode element may preferably, but need not necessarily, include a charge coupled device (CCD) element.

According to an aspect of one preferred embodiment of the invention, preferably in the sensing step, the light source element may preferably, but need not necessarily, include a laser, a light emitting diode (LED), an optical fiber light source element, a tungsten lamp, a mercury lamp, and/or a xenon lamp.

According to an aspect of one preferred embodiment of the invention, the method may preferably, but need not necessarily, also includes a storage step, preferably after the sensing step, of using the algorithms to enable the electronic device processor to store the presentation data and/or the test data in an electronic device memory onboard the electronic device.

According to an aspect of one preferred embodiment of the invention, preferably in the presentation step, the presentation element may preferably, but need not necessarily, include a display element. The algorithms may preferably, but need not necessarily, enable the electronic device processor to generate the presentation data for presentation from the display element, preferably in the form of one or more visually presentable (a) textual data, (b) graphical data, and/or (c) colored indicator light data.

According to an aspect of one preferred embodiment of the invention, the method may preferably, but need not necessarily, also include a powering step, preferably before the uploading step, of using a test device battery onboard the test device to power the test device.

According to an aspect of one preferred embodiment of the invention, the method may preferably, but need not necessarily, also include a powering step, preferably before the uploading step, of using an electronic device battery onboard the electronic device to transmit power to the test connection element of the test device, preferably via the electronic connection element.

According to an aspect of one preferred embodiment of the invention, preferably in the connecting step, one or more of following may preferably, but need not necessarily, be used as the electronic device: (a) a cellular telephone; (b) a mobile communications device; (c) a personal digital assistant; (d) a desktop computer; (e) a laptop computer; (f) a navigation device; (g) a digital audio player; (h) a camera; (i) a gaming device; (j) a television; and/or (k) a radio.

Other advantages, features and characteristics of the present invention, as well as methods of operation and functions of the related elements of the method and device, and the combination of steps, parts and economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the device and method according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

Figure 1A:
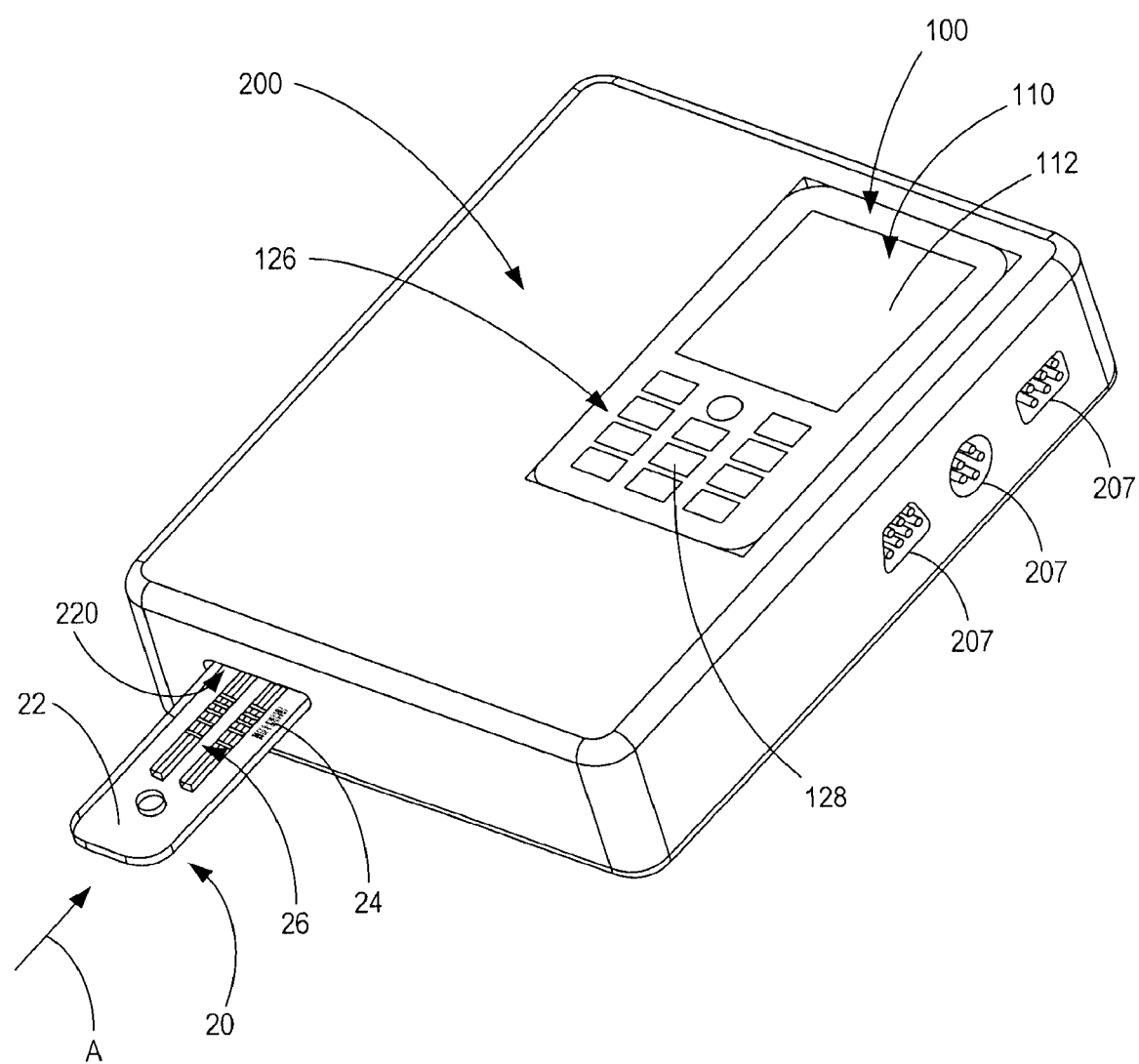
FIG. 1A is a top front perspective view of a test device and integral electronic device according to one preferred embodiment of the invention.

In FIGS. 1A to 7, there is shown a handheld diagnostic test device 200 and methods 500, 600 according to the present invention. The test device 200 is for use with an electronic device 100 and a test cartridge 20 carrying a biological and/or environmental test sample for reaction with one or more reagents in a rapid diagnostic test. The test cartridge 20 preferably provides components needed for performing the reaction, such as, the reagents and a sample support 22 (e.g., slide, substrate) or platform for incubation.

The test device 200 may preferably, according to the invention, be linked with more than one different type of electronic device 100, and more preferably with a wide range of different types of electronic devices 100. The electronic device 100 may be a cellular telephone (as shown in FIGS. 1A to 2). According to various other preferred embodiments of the invention, the electronic device 100 may take the form of a mobile communications device (e.g., a smart phone and/or a radio-frequency chipset device), a personal digital assistant, a pocket PC, a laptop computer, a desktop computer, a navigation device, a digital audio player, a camera, a gaming device, a television, and/or a radio. According to some preferred embodiments of the invention, it may be suitable to utilize any electronic device 100 which provides a power source, a display element, a data input device, and/or the CPU capacity to run, analyze, record and/or transmit the test results.

Figure 1B:
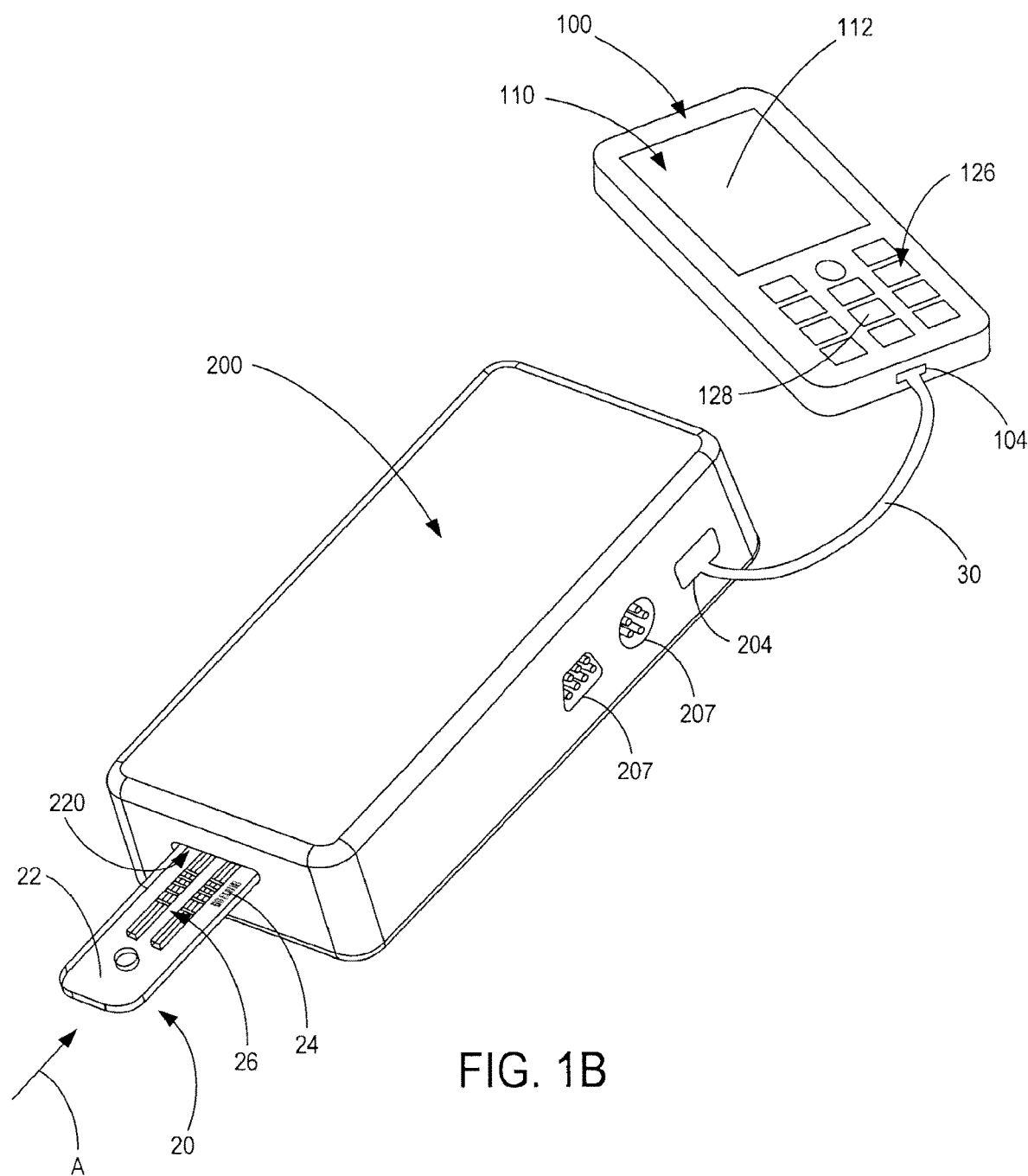
FIG. 1B is a top front perspective view of a test device and connected electronic device according to another preferred embodiment of the invention.
Figure 2:
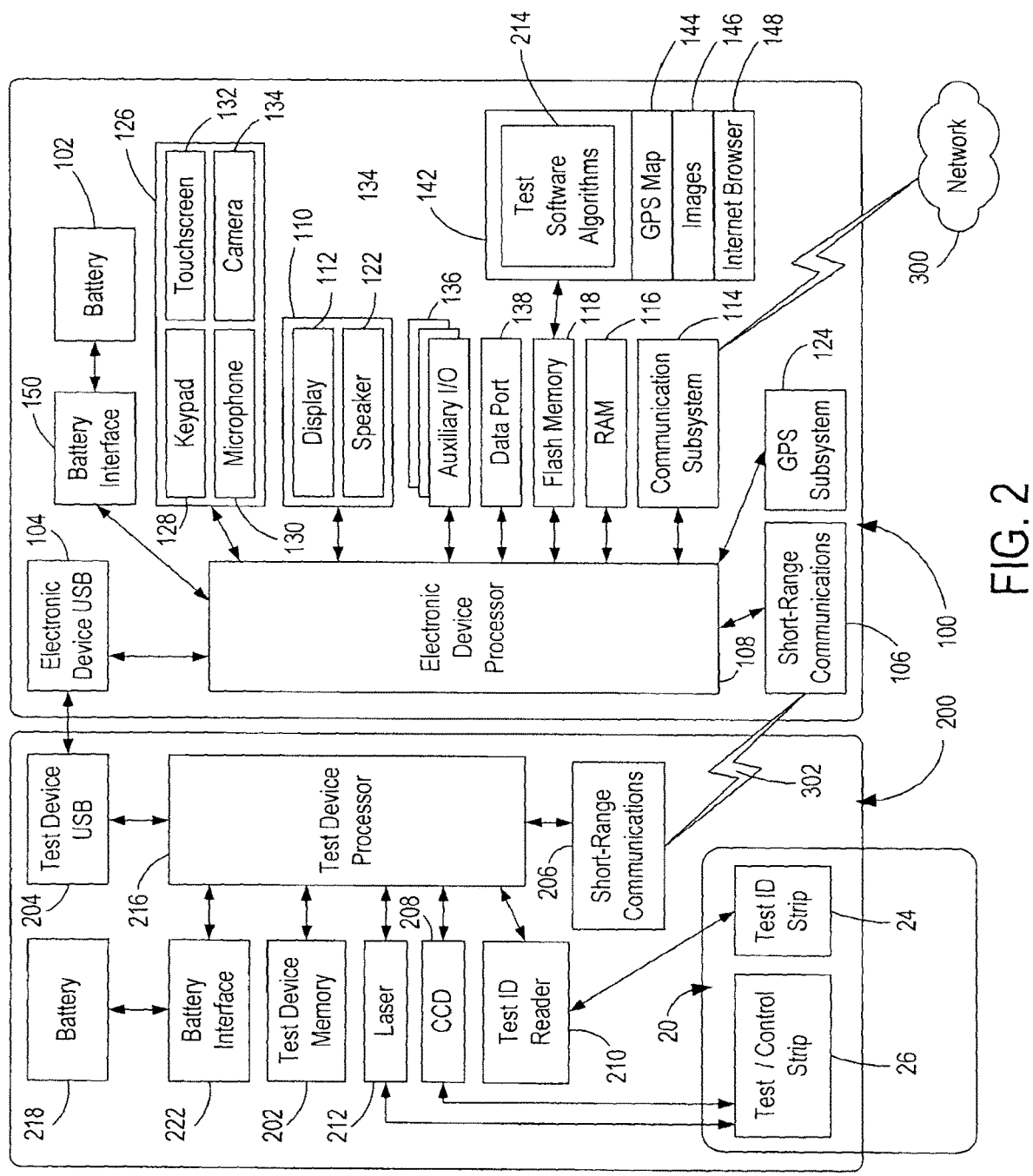
FIG. 2 is a schematic diagram of the test device and electronic device of FIG. 1B.

Preferably, as best seen in FIGS. 1A and 1B, the test device 200 is for use with the electronic device 100, and is provided with a test cartridge port 220 adapted to receive the test cartridge 20 for operative reaction of the sample with the reagents. As shown in FIG. 2, the test device 200 preferably has onboard memory 202 to provide electronic data storage capacity, one or more test device connection elements 204, 206, 207 for communicating with the electronic device 100, and one or more sensors 208, 210 for performing a measurement or detection.

Depending on the technology used for detection, the sensors 208, 210 may preferably, and by way of a non-limiting example, be optical in nature (e.g., relying on fluorescence or colorimetry) or electrical in nature (e.g., relying on impedance effects). Preferably, many different detection technologies may be capable of use within the test device 200 (and which may be capable of modification in function, in the discoveries made, and/or in the detection field), such as, for example and among other things, one or more of the following: lateral flow strip detection technologies; nano and/or micro cytometer detection technologies; impedance sensor detection technologies; dieletrophoresis detection technologies; micro PCR detection technologies; and/or electro peptide sensor technologies.

The sensors 208, 210 preferably receive a signal which is preferably transferred through data acquisition components so as to be sent, as is described in greater detail hereinbelow, to the electronic device 100. (In some alternate embodiments of the invention, optical fiber output or diode sensors may be used within the electronic device 100 as an excitation and/or optical sensor in place of, or in addition to, the sensors 208, 210 of the test device 200. Preferably, however, the sensors 208, 210 are provided as part of the test device 200.)

As shown in FIG. 2, the sensors 208, 210 may include a photodiode (e.g., a charge coupled device) 208 and a test identification reader 210. Preferably, the photodiode 208 works together with a light source element (e.g., a laser) 212 of the test device 200 to operatively detect test data from the sample after reaction with the reagents. Notably, the laser 212 which is shown in FIG. 2 is provided according to one preferred embodiment according to the present invention. Alternately, any number of different light source elements 212 might be used instead and/or in addition thereto—for example, a tungsten lamp, a mercury lamp, a xenon lamp, a light emitting diode (LED) and/or an optical fiber light source. Additionally, the charge coupled device 208 shown in FIG. 2 is provided according to one preferred embodiment according to the present invention. Alternately, other types of photodiodes 208, light detectors (e.g., photodetectors) and/or sensors—e.g., a CMOS camera—may be used in place thereof and/or in addition thereto.

According to some preferred embodiments of the invention, the test connection elements 204, 206, 207 may be provided as separate or embedded components of the test device 200. One of the test device connection elements 204, 206, 207 may preferably connect or link the test device 200 with the electronic device 100 to enable communication therewith. The test device connection elements 204, 206, 207 may take the form of a USB port 204 and/or a short-range communications (e.g., Bluetooth) element 206 provided on the test device 200—as shown in FIG. 2. The test device connection elements 204, 206, 207 may assist, facilitate and enable a transfer of data, and optical or electrical pulses. Preferably, at least one of the test device connection elements 204, 206, 207 (e.g., the USB port 204) may assist, facilitate and enable a transfer of energy.

As shown in FIG. 2, the onboard memory 202 may preferably be provided within the test device 200. As is described in greater detail below, the onboard memory 202 may preferably be used to store test software algorithms 214 required to run the test—e.g., including the test method, the quality control data, the analysis process, the GUI interface instructions, and any other software applications or algorithms associated with the test—for data transfer or upload from the test device 200 to the electronic device 100. The onboard memory 202 may preferably also be capable of storing the test data for use later. (In some embodiments of the invention, the onboard memory 202 may preferably also be associated with a test device processor 216, or CPU capability, onboard the test device 200 to assist with or manage data transfer between the test device 200 and the electronic device 100.)

In some embodiments of the invention, and as shown in FIG. 2, the test device 200 may include a battery or power supply 218 and a battery interface 222. This power supply 218 may be provided, for example, in case the electronic device 100 is not capable of supporting the required or preferred power supply demands of the test device 200. That said, the electronic device 100 preferably includes a battery (or power supply) 102 of its own as shown in FIG. 2, which may preferably be sufficient to provide the test device 200 with an energy source.

As shown in FIG. 2, the electronic device 100 preferably also includes one or more electronic device connection elements 104, 106 and an electronic device processor (or CPU capability) 108. The electronic device processor 108 uses the software algorithms 214 to control the rapid diagnostic test.

The electronic device connection elements 104, 106 may preferably include a plug-in interface (e.g., a USB port) 104 as shown in FIG. 2. The electronic device connection elements 104, 106 may preferably be provided as any kind of interfacing element suitable to transfer data to the test device 200. As shown in FIG. 2, one of the electronic device connection elements 104, 106 may take the form of a short-range communications (e.g., Bluetooth) element 106. The interface between the test device 200 and the electronic device 100 may preferably utilize components which meet the connectivity requirements of the electronic device 100.

Preferably, at least one of the electronic device connection elements 104, 106 (e.g., the plug-in interface 104) may be suitable to transfer energy to the test device 200. One of the electronic device connection elements 104, 106 is operatively connected with a respective one of the test connection elements 204, 206, 207 in data communicating relation. According to one preferred embodiment of the invention, the USB ports 104, 204 are connected with one another in mating relation (as best seen in FIG. 1B). Preferably, the USB port 204 of the test device 200 receives power from the battery 102, via the USB port 104, of the electronic device 100. The USB port 104 of the electronic device 100 is preferably capable of transferring the energy and/or power from the battery 102 of the electronic device 100 to the test device 200. According to some preferred embodiments of the invention, the battery 102 of the electronic device may afford a power supply capability to transfer energy which may preferably be sufficient to run the test device 200. Perhaps notably, some electronic devices 100 (e.g., including many common cellular telephones) which are contemplated for use according to the present invention may draw, but not supply, power from their USB port 104. That said, this limitation is not common to all electronic devices 100, nor even to all cellular telephones. As such, and as aforesaid, the test device 200 may preferably be partially and/or fully powered by the electronic device 100.

Preferably, one of the test device connection elements 204, 206, 207 electronically transmits the test data to the electronic device 100 via a respective one of the electronic device connection elements 104, 106. In this manner, at least one of the electronic device connection elements 104, 106 electronically preferably receives the test data from the test device 200.

The electronic device processor 108 may preferably provide enough processing capability to control the test device 200. Preferably, data included in the onboard memory 202 within the test device 200 may detail the minimum requirements, in terms of required processing capability, to run the test device 200. The electronic device processor 108 operatively applies one or more of the algorithms 214 in managing the electronic device 100 and its interface with the test device 200. For example, the algorithms 214 may include device management software and data analysis software.

The device management software may include graphical user interface (GUI) software and a data quality control application. The quality control application is preferably operative to check on the proper functioning of the test device 200 and/or quality assurance data 418 (as may be best appreciated from FIG. 3) associated with the test cartridge 20, or to meet regulation requirements.

According to the invention, the GUI software may preferably assist, facilitate or enable display of presentation data 400 to a user of the electronic device 100. The GUI software may preferably be run, for example, inside a browser (e.g., an Internet browser) 148 and/or through another GUI window.

The data analysis software may include test data processing and diagnostic applications. The test data processing applications may preferably include algorithms to analyze the test data, and a data transfer protocol to enable the electronic device 100 to communicate with or download data from the test device 200. (According to some preferred embodiments of the invention, the electronic device processor 108 may also operatively apply the test data processing applications to control the reaction of the sample with the reagents. Accordingly, by the aforesaid transmission of the test data processing applications and the test data, the test device 200 enables the electronic device processor 108 to, among other things, control the reaction of the sample with the reagents.) The testing of the sample by the test device 200 may be directly initiated by the electronic device processor 108—e.g., by instructing the user to add the sample to the test cartridge 20.

The electronic device processor 108 operatively receives the test data, and applies the test data processing applications to the test data to generate highly sensitive and accurate quantitative and/or qualitative test results and/or presentation data based on the quantitative test data. In so doing, according to some preferred embodiments of the invention, the test results may be quantified as high, medium, and/or low results (e.g., a low intensity of infection result). Perhaps notably, the "highly sensitive and accurate quantitative test results" which are generated according to the present invention have comparable accuracy and sensitivity with those which have been previously quantified in a laboratory or hospital setting. Advantageously, therefore and due in part to the portability inherent in the handheld test device 200 and the electronic device 100, the present invention enables the generation of highly sensitive and accurate quantitative and qualitative test results outside of such laboratory and hospital settings.

It may also be worthwhile to note that the presentation data 400 presented to the user may preferably include treatment and follow-up suggestion data (not shown) based on the test results. The test device 200 is preferably adapted for use with, and to aid in the generation of, such presentation data 400. The treatment and follow-up suggestion data is preferably determined with reference to one or more of the algorithms 214 uploaded to the electronic device 100 or stored on the test device 200, or in remote and/or distributed databases and/or servers (not shown).

Preferably, the onboard memory 202 of the test device 200 electronically stores the test data and one or more of the algorithms 214. Preferably, one of the test device connection elements 204, 206, 207 electronically transmits the algorithms 214 to a corresponding one of the electronic device connection elements 104, 106. In this manner, the electronic device processor 108 operatively receives the algorithms 214 from the test device 200 via the test and electronic device connection elements, 204, 206, 207 and 104, 106 respectively.

As shown in FIG. 2, the electronic device 100 preferably also has a presentation element 110, and further connectivity components. As shown in FIGS. 1A to 3, the presentation element 110 preferably includes a display element 112 which has a display capability (e.g., a display screen and/or a printer) and/or which offers a graphical user interface (or GUI). Preferably, the algorithms 214 generate the quantitative and/or qualitative test results and/or the presentation data for presentation by the electronic device 100 in the form of visually and/or audibly presentable data. Audibly presentable data may take the form of a verbal, musical, tonal and/or other alert sounds.

Figure 3:
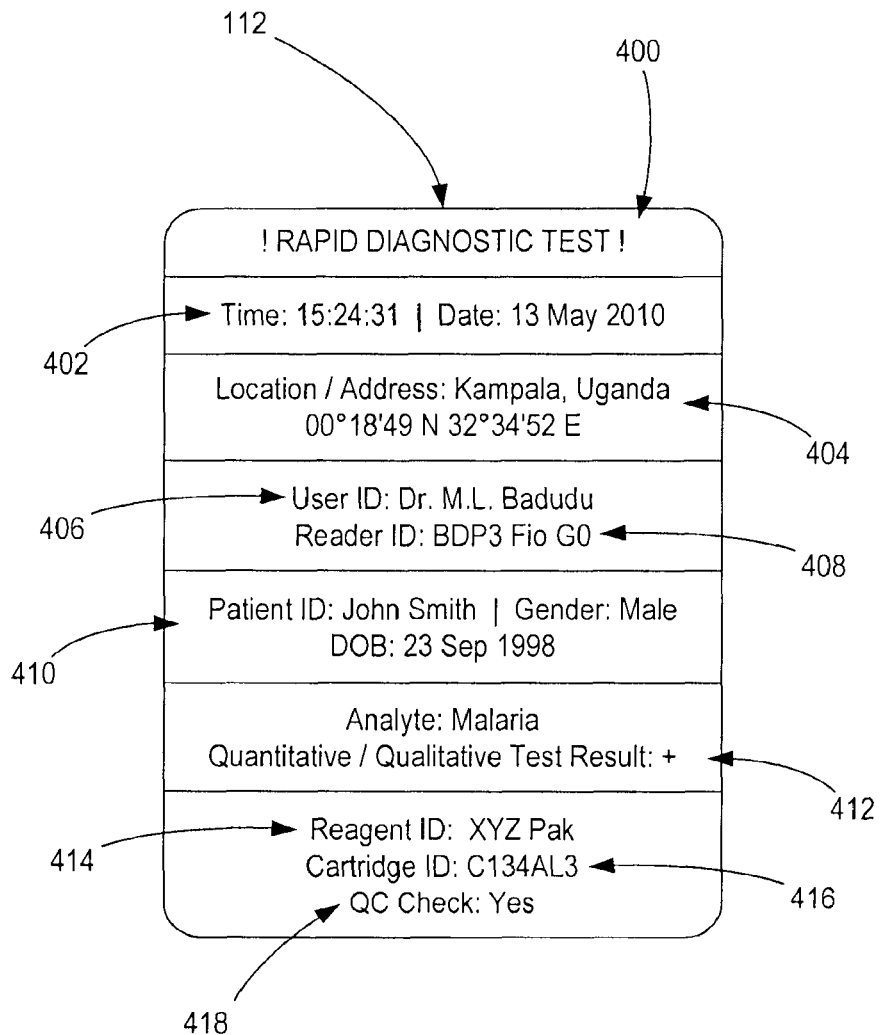
FIG. 3 is a graphic representation of data presented from a display of the electronic device of FIG. 1A or 1B according to the invention.
Figure 4:
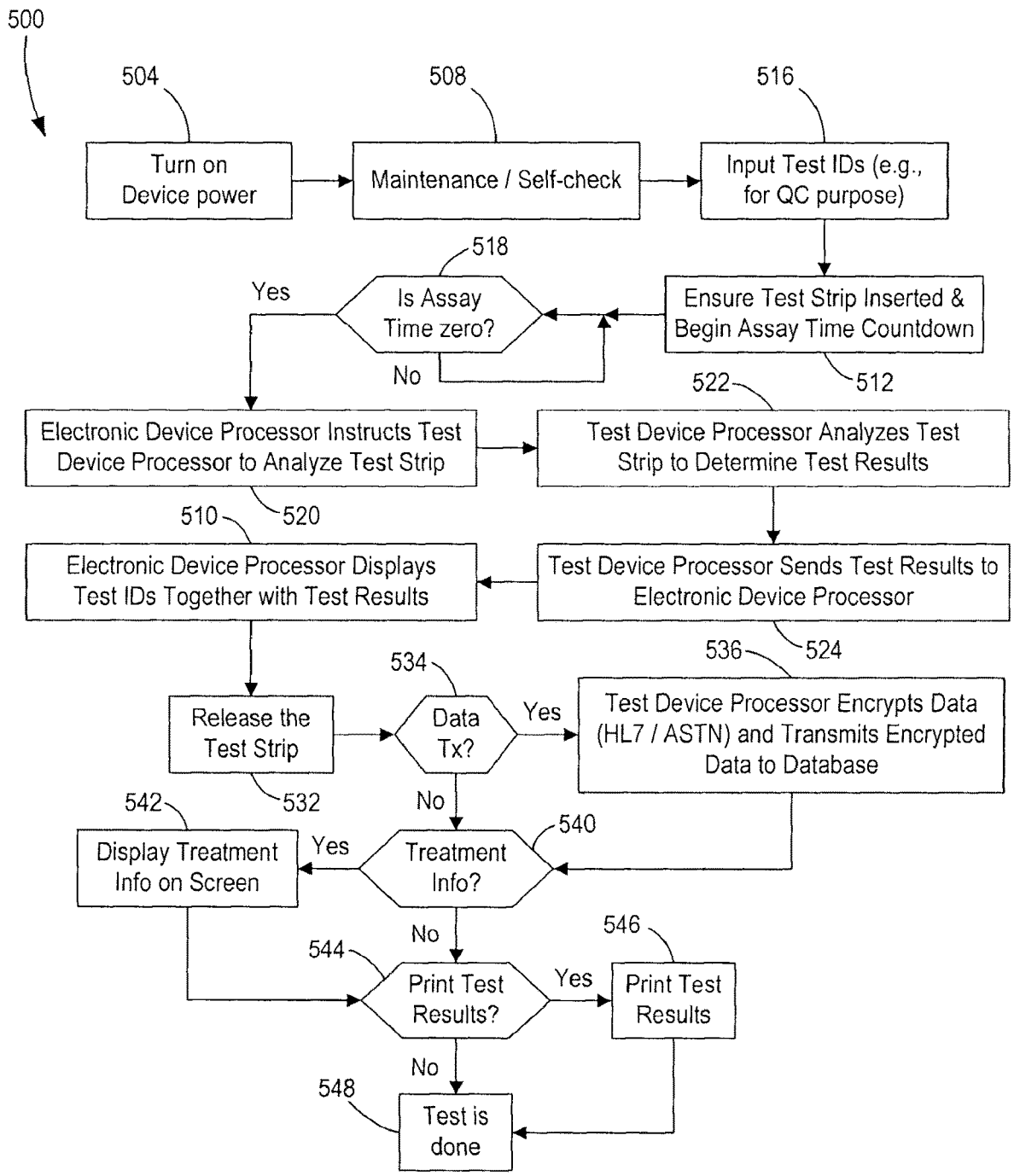
FIG. 4 is a flowchart of one illustrative method according to the invention.

Visually presentable data may take the form of text, graphics and/or colored indicator lights. FIG. 3 illustrates one form of visually presentable data which is contemplated according to the present invention, namely, visually presentable textual data. Among other things, the display element 112 might also present graphical data which may include charts and other comparative visual representations of the quantitative test results. By way of example, and among other things, visually and/or audibly presentable data may also include descriptive and/or numerical data. Exemplary types of descriptive data may include the treatment and follow-up suggestion data and/or intensity information. Intensity data may be shown in textual and/or graphical format. Exemplary types of numerical data may include the quantitative test results. Other visually presentable data may include textual data, and/or colored indicator light data. Preferably, the display element 112 enables display of the presentation data 400. (In some embodiments of the invention, a printer, a speaker 122 onboard the electronic device 100 or other kinds of output systems are used for visualization or presentation.) The presentation element 110 operatively presents the presentation data 400 to the user. Accordingly, by the aforesaid transmission of the test data processing applications and the test data, the test device 200 also enables generation and presentation of the presentation data 400 by the electronic device processor 108 and the presentation element 110.

The electronic device 100 is preferably a networking electronic device and is provided with a communication subsystem 114 to afford connectivity and/or communications (e.g., network connection, GSM, satellite connection, Internet) capabilities. As shown in FIG. 2, the communication subsystem 114 networks with an external network 300 which may be a satellite network (e.g., GPS networks), a terrestrial wireless network (e.g., a cellular telephone network, a local wireless network), the Internet, and/or a laboratory and/or hospital information system network. The electronic device 100 may preferably be in wireless (and/or wired) communication with at least one external network 300.

The communication subsystem 114 which is provided may preferably depend on the type or version of the electronic device 100. In the case of a cellular telephone, for example, its wireless capability may be used to transmit data via a cellular telephone network to one of the remote databases. In the case of a laptop (or pocket PC), the communication subsystem 114 may preferably be an intranet connection, or a wired or wireless Internet connection.

The electronic device 100 may preferably also have the ability to connect quickly and easily to LIS/HIS networks via, for example, the local wireless network (e.g., a Bluetooth network) and/or a USB cable. Preferably, the electronic device 100 automatically transmits the test data, the presentation data 400 (e.g., test results 412) and/or encrypted data 426 for recordal in one or more remote and/or distributed databases or servers (e.g., in a LIS/HIS network). Additionally, transmission of the test data, the presentation data 400 (e.g., the test results 412) and/or the encrypted data 426 by the electronic device 100, via the communication subsystem 114 over the network 300, may be initiated directly and/or indirectly by the user by controlling a dedicated button or a context dependent programmable button or key. Preferably, the electronic device 100 may be provided with an electronic device memory (e.g., a flash memory) 118 which is able to record the test results 412 related to each test. The remote and/or distributed databases and/or servers may also be used for various tests or patients and are preferably linkable with the data stored on the electronic device 100.

Various databases may interface with the communications subsystem 114, preferably including, software applications databases (e.g., clinical software applications, database software applications, download portals, quality control central databases), and various test result databases (e.g., healthcare providers database, governmental agency databases, military department databases). Notably, the databases may include, without limitation, epidemiologic databases, UN and major/international healthcare institution databases, healthcare and emergency infrastructure databases, education and economic databases, news databases, demographic databases, communication and military infrastructure databases, and weather and topographic databases. The databases may preferably serve as an additional repository for the test results 412 (test result databases), and/or as an additional source for the electronic device to acquire the algorithms 214 and/or updates to the algorithms 214 (e.g., test processing algorithms and software applications)—i.e., from software applications databases.

Communication functions, including data and voice communications, may be performed through the communication subsystem 114. The communication subsystem 114 preferably acts as both a receiving element and a transmitting element.

As shown in FIG. 2, the test device 200 and/or the electronic device processor 108 may also interact with additional subsystems of the electronic device 100, such as a random access memory (RAM) 116, the flash memory 118, other presentation elements (e.g., the speaker 122), the short-range communications system 106, a GPS subsystem 124, a data input device 126 (e.g., a keypad 128, a trackball, a microphone 130, a touchscreen 132, a camera 134), one or more auxiliary input/outputs 136, and/or a data port 138. Operating system software for the standard functions of the electronic device 100 used by the electronic device processor 108 may typically be stored in a persistent store such as the flash memory 118. Specific device applications 142 may also be stored in the flash memory 118 and may include GPS map applications 144 and image related applications 146, among others. Those skilled in the art will appreciate that the operating system, specific device applications, or parts thereof, may be temporarily loaded into a volatile store, such as the RAM 116, for processing by electronic device processor 108.

FIG. 1A depicts the diagnostic test device (alternately herein, a "test reader" or "diagnostic reader") 200 with the electronic device 100 integrated therein. In FIG. 1A, the electronic device 100 is shown integrally embedded in a cavity formed in a housing of the test device 200. The physical connection between the electronic device 100 and the test device 200 may include a "plug-in-plug", cabled, wired, and/or hardwired connection. Preferably, though not necessarily, the data communication link between the electronic device 100 and the test device 200 may be selectively severed and/or disconnected. Preferably, though not necessarily, the electronic device 100 may be selectively removable (i.e., physically) from the test device 200. Alternately, as shown in FIG. 1B, it is within the scope of the present invention for the electronic device 100 to be physically connected to, but located outside of, the test device by way of a "plug-in-plug", cabled, and/or wired connection. Still further, and though not shown in the accompanying drawings, it is within the scope of the present invention for the electronic device 100 to be wirelessly connected to and located remotely of the test device 200, with the connection between the two being a wireless data communication connection 302 (best shown in FIG. 2). That is, the test device 200 and the electronic device 100 may be located remotely of one another, with the sole connection between the two being the wireless data communication connection 302. The test device 200 and electronic device may preferably be connected to one another via the USB ports 104, 204 and/or via any available port able to provide data transfer and/or energy supply (including Bluetooth in case the device is not physically integrated in with the reader, but rather communicates from a distance).

Preferably, when the electronic device 100 is a networking electronic device, it remains at least partially, and more preferably fully, functional as such. The test device 200 may preferably be controlled via the electronic device 100. Little or no modification of the hardware of the electronic device 100 is required.

Preferably, the algorithms 214 are operatively loaded onto the electronic device 100. The electronic device 100 may preferably be provided (natively and/or when it is operatively loaded with the algorithms 214) with the browser 148. A keypad (alternately herein a "keyboard") 126 and/or the display element 112 of the electronic device 100 may preferably be utilized in association with the test device 200 and/or the algorithms 214.

As shown in FIG. 2, the battery 102 of the electronic device 100 is preferably provided with a battery interface 150 utilized and may be provided with a smart power management function. Power management of the test 200 device may be effected in numerous different ways according to the present invention. The test device 200 may power itself, it may be powered by the electronic device 100, or it may be powered both by itself and by the electronic device 100.

The test device 200 (together with the electronic device 100) and the methods 500, 600 which are provided according to the present invention are preferably adapted for use in association with infectious disease surveillance, diagnosis and emergency medical response at the point of care in developed and developing countries, refugee camps, etc.

The test device 200 (together with the electronic device 100) and the methods 500, 600 which are provided according to the present invention are preferably adapted to rapidly perform quantitative and/or qualitative diagnostic tests, and to enable assay time counting, among other things. It will be appreciated from the disclosures herein that the test device 200 and the methods 500, 600 are preferably be available for deployment and/or purchase at a reasonable price—i.e., a potentially important factor in many of the areas of the world where infectious disease surveillance may be of primary concern.

As aforesaid, the electronic device 100 is preferably a networking electronic device. It is preferably equipped with a global communication capability (e.g., according to a GSM and/or GPRS protocol), and with a location tracking capability via a geo-localization element (e.g., a global location tracking element and/or a GPS subsystem) 140 provided onboard the electronic device 100.

As described elsewhere herein, the test device 200 (together with the electronic device 100) and the methods 500, 600 are preferably adapted to enable smart patient data management, in full compliance with all applicable interface standards for exchanging and/or transferring health data—e.g., the HL7 and/or ASTM standards.

As best shown in FIGS. 1A to 2, the test cartridge (alternately herein the "test cassette" and/or "test strip") 20 may preferably be provided with a test cartridge identification element (alternately herein the "test ID strip") 24—for example, a barcode as shown in FIGS. 1A and 1B. Alternately, though not shown in the accompanying drawings, the test cartridge identification element 24 may be a radio-frequency identification (RFID) tag. The test cartridge identification element 24 enables identification of the test cartridge 20. Preferably, before analysis of the sample and/or before conclusion of its reaction with the reagents, the test cartridge 20 is identified using data associated with the test cartridge identification element (e.g., barcode and/or RFID tag) 24.

Use of the test cartridge identification element 24 enables certain quality control (QC) and/or quality assurance (QA) features according to the present invention. For example, assay quality control data 418 and other test cartridge identification data 416 is preferably encoded by the test cartridge identification element 24. Preferably, but not necessarily, the test cartridge identification data 416 includes cassette ID, lot number, expired data, assay cut-off, assay calibration curves, etc. In the case of the barcode 24, it may preferably be positioned beside test and control strips (or lines) 26. The barcode 24 and the test and control lines 26 may preferably, but need not necessarily, be captured in one image by the charge-coupled device (CCD) 208 or by a camera. The quality control data 418 may preferably be required before making any diagnostic decision. During image processing, the quality control data 418 encoded by the barcode 24 is preferably decoded first, with the test results 412 being thereafter calculated.

Ideally, the above-described combination of the test device 200 and the electronic device 100 may preferably allow a patient and/or healthcare provider to readily perform—preferably at their fingertips and/or in the palm of their hand—one or more diagnostic tests with substantially the same analytic capability as other substantially more unwieldy prior art high-tech diagnostic devices.

Preferably, and as aforesaid, some preferred embodiments of the invention may involve use of a mobile or cellular telephone as the electronic device 100—i.e., in association with the test device 200.

As best seen in FIG. 1B, according to some embodiments of the invention, the test device 200 may also be connected with the electronic device via a USB cable 30 and the USB ports 104, 204 and/or via any other available port to provide data transfer and/or energy supply. Similarly, though not shown in the drawings, the test device 200 may be used with a laptop computer, a desktop computer and/or a pocket PC according to the present invention. As in the case of the electronic device 100 (discussed above), the test device 200 may also be connected with the laptop computer, the desktop computer and/or pocket PC via a USB port and/or via any other available port to provide data transfer and/or energy supply.

With reference to the various embodiments of the system 100 which are shown in the drawings, it will be appreciated by one skilled in the art that, although some components, relations, processes and aspects of same are only discussed with reference to one or more specific drawings, same may be used and/or adapted for use in association with embodiments shown in other ones of the drawings.

FIGS. 4 and 5A-5D show, schematically by way of overview, two preferred methods 500, 600 of testing the sample, for use with the reagents, the electronic device 100, and the test device 200. The methods 500, 600 preferably include the following steps, among others: a connecting step (not shown); a powering step 504, 604; an uploading step (not shown) after the connecting step and the powering step 504, 604; a maintenance step 508, 608 after the uploading step; a presentation step 510, 610 after the uploading step; a cartridge inserting step 512, 612 after the connecting step and the uploading step; a data input step 516, 616 after the uploading step; a cartridge identification step (not shown); a waiting step 518, 618; a sensing step 520, 620 after the waiting step 518, 618 and the cartridge inserting step 512, 612; a test device processing step 522, 622; a geo-localization step (not shown); one or more electronic device processing steps 625, 626, 628 after the cartridge identification step 614, the sensing step 520, 620 and the test device processing step 522, 622; an encryption step (see method steps 536, 636 in FIGS. 5D and 6) after the data input step 516, 616; a storage step 630 after the sensing step 520, 620; and/or a networking step 536, 636 after the geo-localization step, the electronic device processing steps 625, 626, 628 and the encryption step.

In the connecting step (not shown), at least one of the test connection elements 204, 206, 207 establishes a connection with the electronic device 100. According to some preferred embodiments of the invention, one of the electronic device connection elements (e.g., the USB port) 104 may be plugged in and/or physically connected, in mating relation, with the test device 200. As best shown in FIG. 1A, the physical connection may be such as to integrally provide the electronic device 100 partially or wholly within a housing of the test device 200. Alternately, as shown in FIG. 1B, the USB cable 30 or other connectivity interface element may preferably be plugged into the test device 200. The USB cable 30 may be considered to be part of the test device 200, the electronic device 100, or a standalone component.

The powering step 504, 604 preferably occurs after the connecting step. In the powering step, one of the test device connection elements (e.g., the USB port) 204 is preferably used to receive, via one of the electronic device connection elements (e.g., the USB port) 104, power from the electronic device battery 102 via a battery interface 150 onboard the electronic device 100. In the powering step 504, 604, after the uploading step (which is described in greater detail hereinbelow), the user may selectively turn on the power for the test device 200, and/or awake the test device 200 from standby mode, using the electronic device 100).

The uploading step (not shown) occurs after the connecting step and preferably before the maintenance step 508, 608, the presentation step 510, 610, the cartridge preparation steps 611a, 611b, the cartridge inserting step 512, 612, the cartridge identification step 614, and the data input step 516, 616, among others. In the uploading step, the test device 200 preferably transfers, to the electronic device 100, some data concerning use of the test device 200 and one or more of the algorithms 214 to process and/or analyze test data using the electronic device 100. That is, in the uploading step, the algorithms 214 are electronically transmitted to the electronic device processor 108, via one of the electronic device connection elements 104, 106, using one of the test device connection elements 204, 206, 207 of the test device 200.

In the maintenance step 508, 608, the test device 200 may preferably perform a self-check (e.g., LED power and some key components), calibration and/or maintenance routine. The maintenance step 508, 608 may preferably be initiated by the electronic device 100. The test device 200 may then indicate whether or not it is ready to the electronic device 100. The maintenance step 508, 608, may also include a self-checking process performed by the electronic device 100. The self-checking performed by the electronic device 100 may include a network signal query 100 which returns a yes/no result indicating whether or not the electronic device is ready for the networking step 536. 636. It may be worthwhile to additionally note that data may be sent from the electronic device 100 to the test device 200 to re-calibrate the test device 200. This data may also include information on the type of test to be run, and the test device 200 could then use this data to cross-correlate with information from the test cartridge 20 to ensure the correct test is run and/or to change the calibration routine, the length of the test, the length of excitation exposure, etc.

Figure 5A:
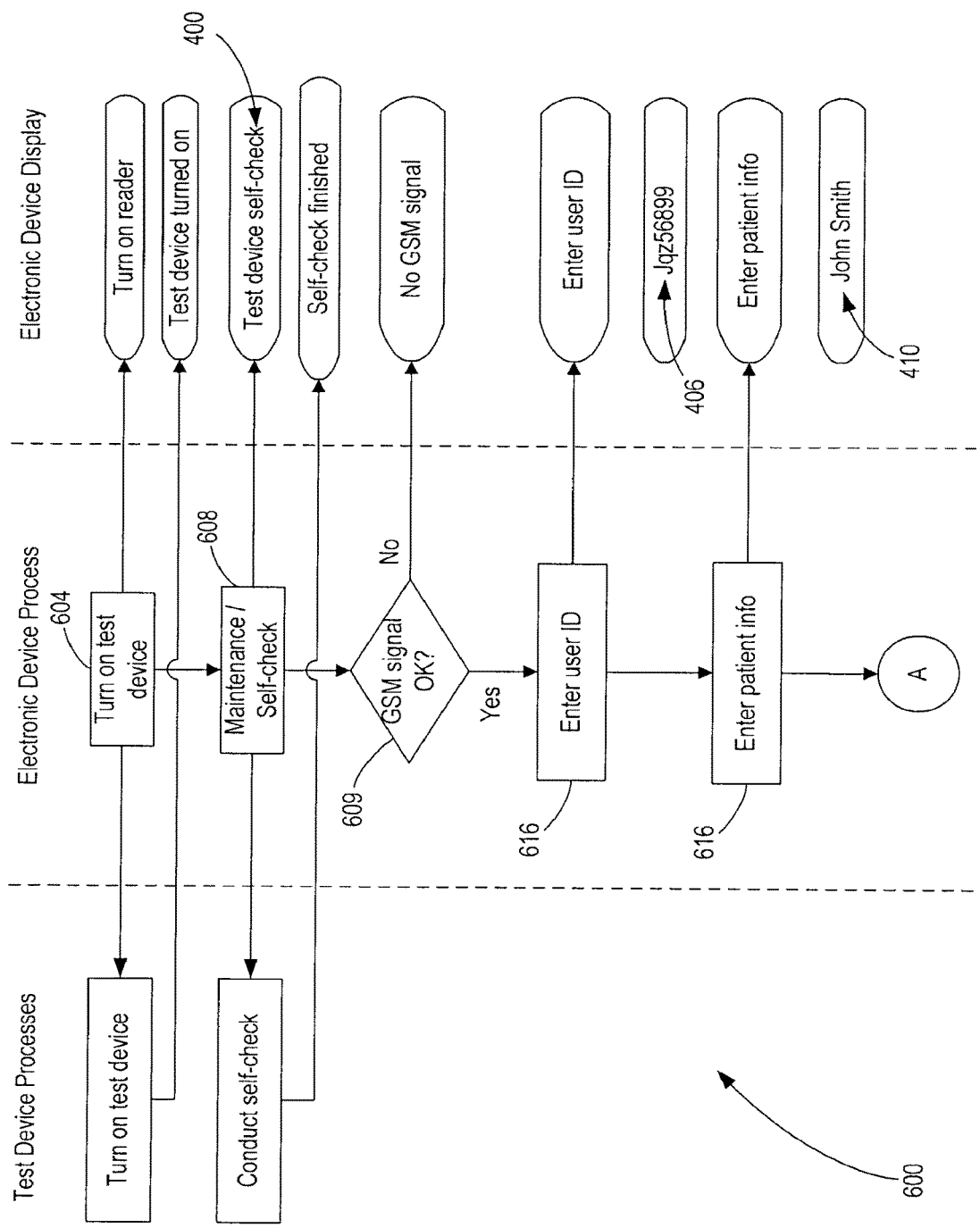
FIGS. 5A to 5D, taken together, are a flowchart of another illustrative method according to the invention.
Figure 5B:
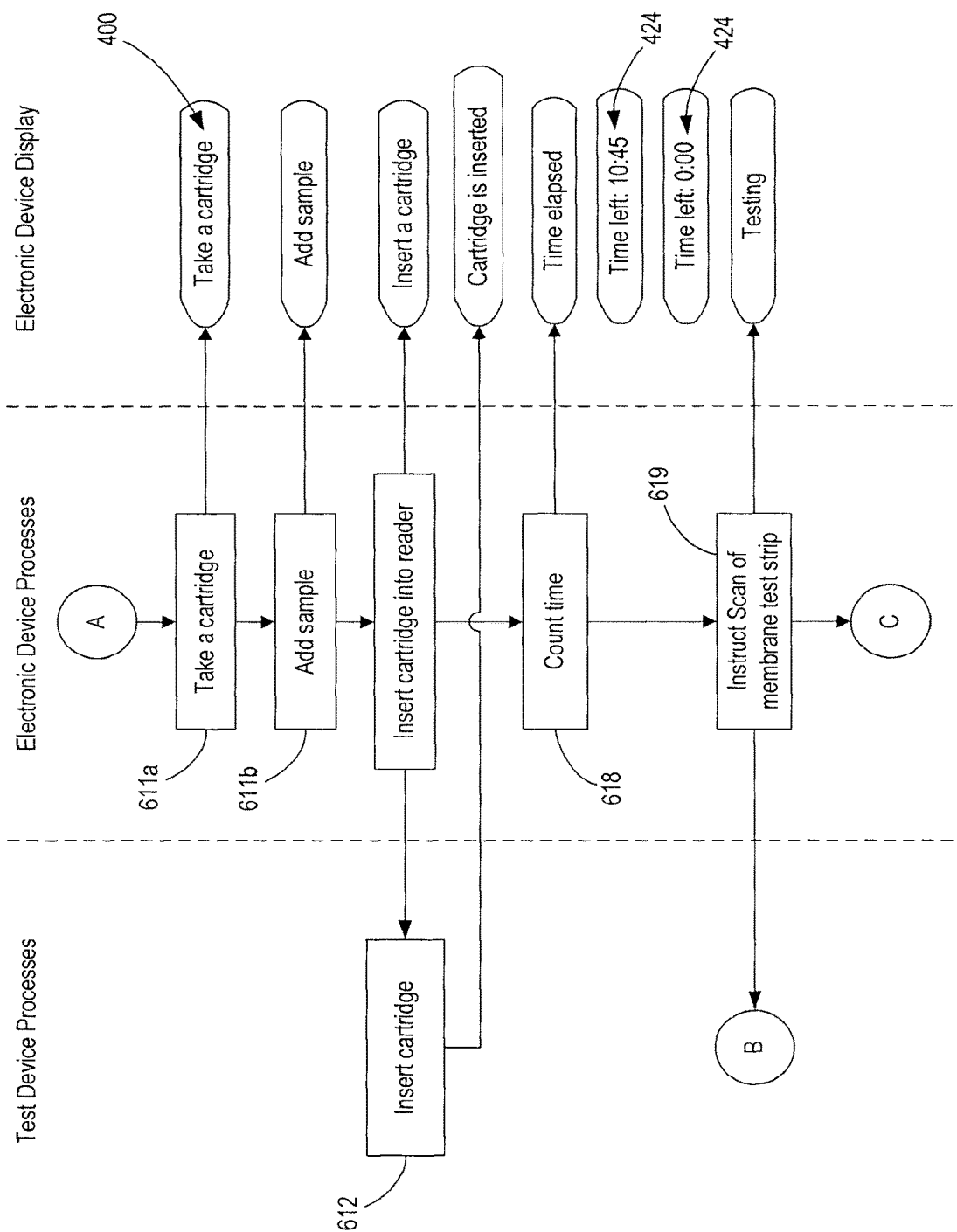
Figure 5C:
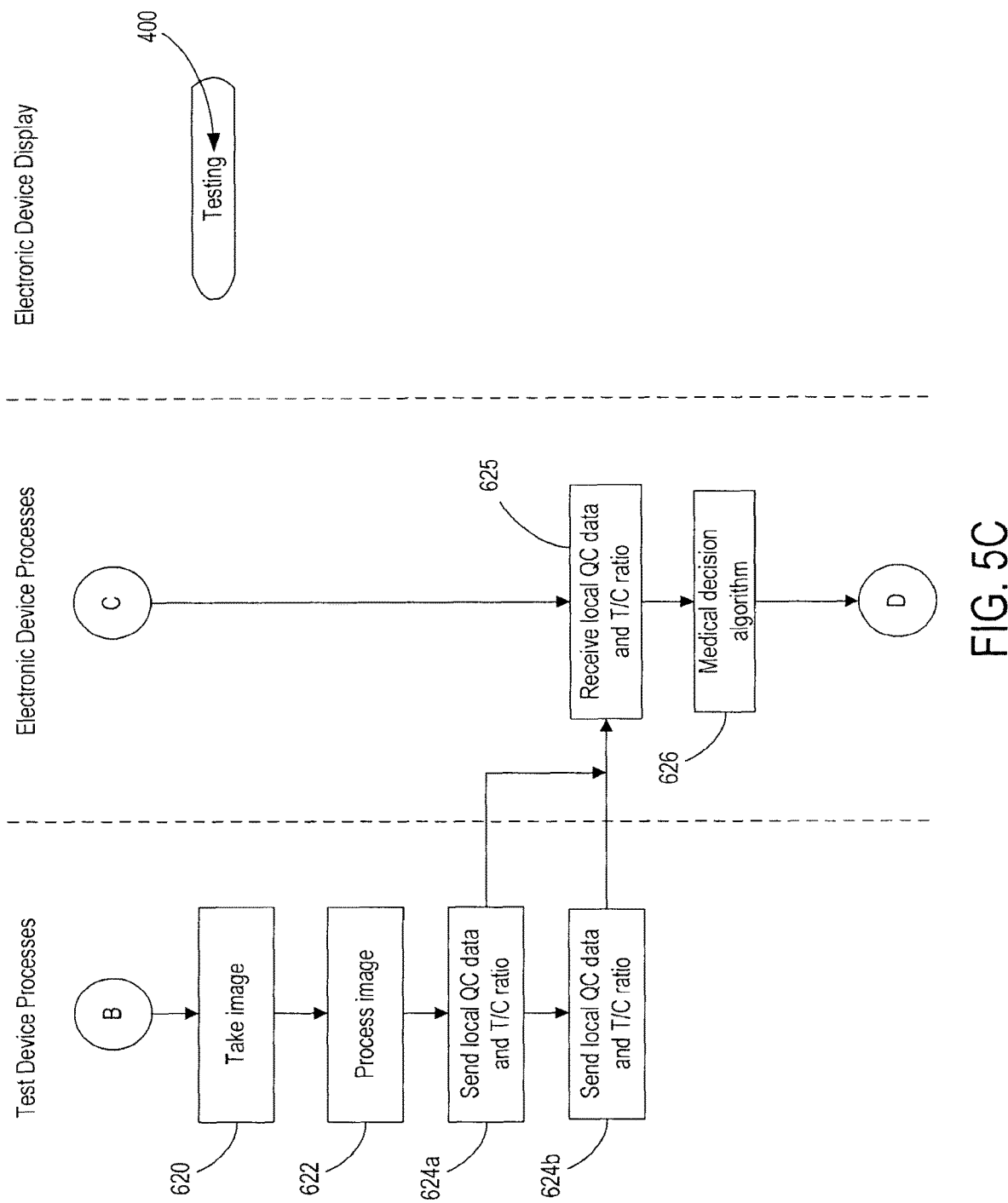
Figure 5D:
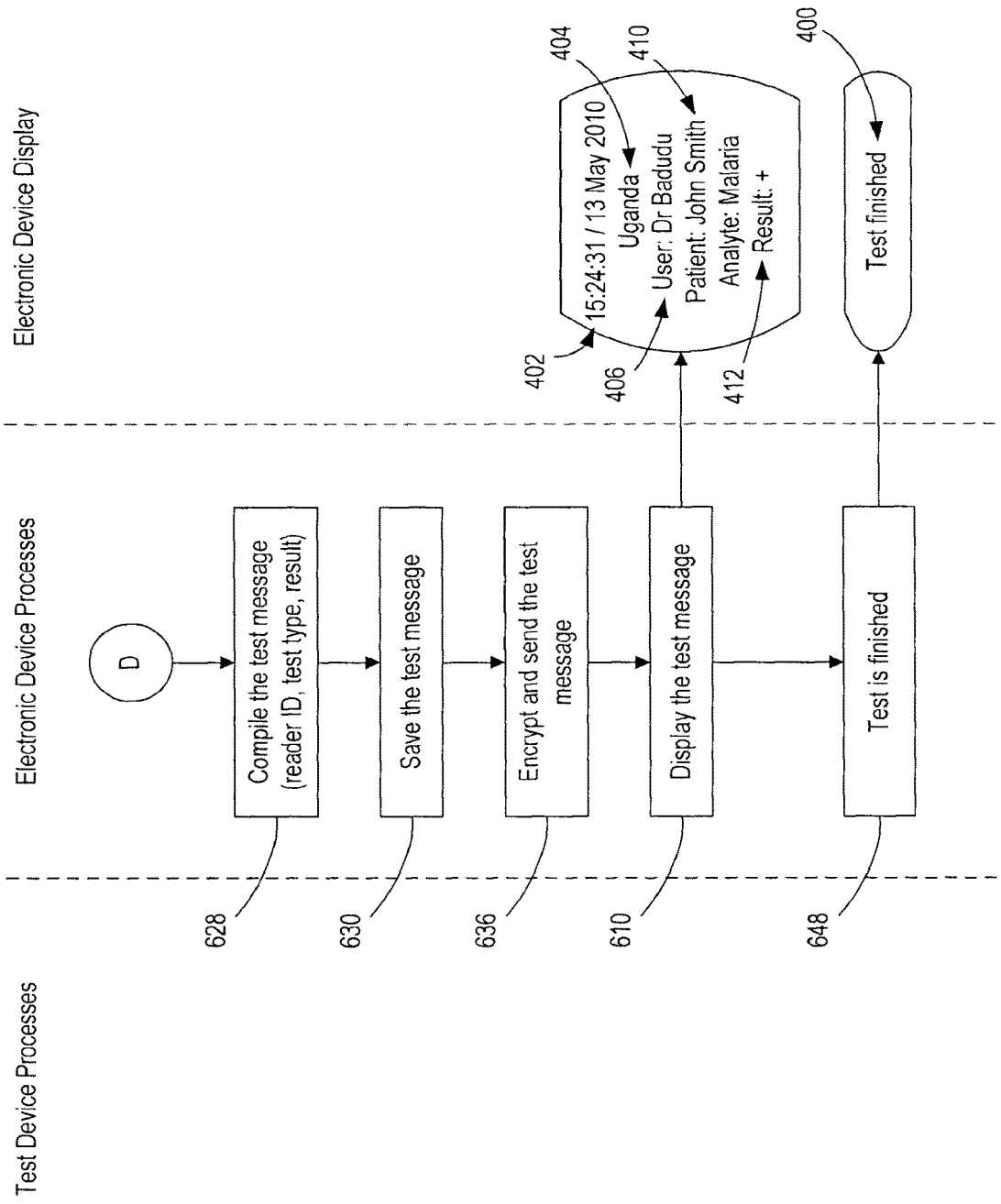

The sample is collected and loaded onto the test cartridge 20 in one or more cartridge preparation steps 611a, 611b (as shown in FIG. 5B). In a cartridge inserting step 512, 612, the user (e.g., a patient, nurse and/or doctor) may preferably then insert the test cartridge 20 in a test cartridge insertion direction as indicated by arrow "A" in FIGS. 1A and 1B, into the test cartridge port 220 of the test device 200.

Prior to the cartridge inserting step, in cartridge preparation steps 611a, 611b, the electronic device 100 may (using its presentation element 110) present instructions to the user concerning preparation of the cartridge 20—e.g., "Take Cartridge" in cartridge preparation step 611a, and "Add Sample" in cartridge preparation step 611b. In the cartridge inserting step 512, 612, the user may selectively insert the test cartridge 20 into the test device 200 for analysis.

In the data input step 516, 616, the electronic device 100 is used to store user identification data 406 associated with the user and/or an owner of the electronic device 100, and/or patient identification data 410 associated with the host from whence the sample was collected. Preferably in the data input step 516, 616, the patient or user may preferably record his or her ID information directly through the keypad 128 of the electronic device 100, or through the camera 134, the touchscreen 132, or the microphone 130 which may be provided in association with the electronic device 100. In the data input step 516, 616, using the electronic device 100 (e.g., keyboard, display), before and/or during the assay, the user may input one or more of the following: a patient ID 410, an address, a user ID 406, a reagent ID 414, a reader ID 408, etc.

In the cartridge identification step (not shown), the test cartridge ID data 416 including the quality assurance information 418 is read from the cartridge ID element 24 of the test cartridge 20. During image analysis, the quality assurance information 418 is preferably decoded before the test data from the test and control strips 26. If the decoded quality assurance information 418 indicates that the test cartridge 20 is expired, then according to a preferred embodiment of the invention, no test results 412 will be presented from the electronic device 100.

In the waiting step 518, 618, after receiving confirmation of the commencement of the reaction of the sample with the reagents (preferably, but not necessarily, via insertion of the test cartridge 20 into the test device 200), the electronic device 100 may then begin an assay time-counting function wherein time counting data 424 is presented to the user from the presentation element 110 in the form of an "Elapsed Time" and/or "Time Remaining". Preferably, this information is displayed on the display element 112 of the electronic device 100. Preferably, by no later than when the "Time Remaining" equals zero, the test will be automatically completed.

Thereafter, the electronic device processor 108 preferably sends a request or instruction to the test device processor 216 for sensing and analysis of the test. (Alternately, the electronic device processor 108 might be utilized for analysis according to the present invention, with the electronic device processor 108 sending the aforesaid request directly to one or more of the sensors 208, 210.) Test detection may, for example, involve fluorescence of the test and control strips 26. Preferably, however, many different types of detection technologies may be capable of use as a detection platform inside of the test device 200. The sending of the aforesaid request or instruction by the electronic device processor 108 is preferably operative, in the sensing step 520, 620, to activate at least one of sensors 208, 210 (e.g., to open an electronic shutter in the CCD 208 to take an image of the test and control strips 26) so as to detect the test data from the test cartridge 20. It is additionally contemplated that the camera 134 of the electronic device 100 might be used as the detection device.

In the test device processing step 522, 622, image analysis and/or biomarker (e.g., pathogen) concentration calculation may preferably be performed by the test device processor 216. In this manner, and since the test device processor 216 may thus provide the test results 412 and interpretation, the time required for regulatory approval of the test device 200 (e.g., by the U.S. Food and Drug Administration or FDA) may be substantially and advantageously reduced.

The methods may also include a test device storage step (not shown) which may preferably occur before test device transmission step 524, 624a, 624b. In the test device storage step, the test data may preferably be electronically stored using the onboard memory 202 of the test device 200. In the test device transmission step 524, 624a, 624b, the test device processor 216 may preferably transmit the test data and/or the test results 412 to the electronic device processor 108—e.g., via a USB interface—for subsequent display to the user by the electronic device display element 112.

In the electronic device processing steps 625, 626, 628, the electronic device 100 may preferably (according to some preferred embodiments of the invention) receive and analyze test data—and/or the test results 412 in some preferred embodiments of the invention—for subsequent presentation of the data to the user. That is, in the processing steps 625, 626, 628, one or more of the algorithms 214 may preferably be applied to the test data and/or to the test results 412 using the processor 108 of the electronic device 100 to generate either the test results 412 and/or the presentation data 400 based on the test results 412. The presentation data 400 so generated preferably includes the treatment and follow-up suggestion data based on the test results 412. As aforesaid, the treatment and follow-up suggestion data is preferably determined with reference to one or more of the algorithms 214 stored onboard the electronic device 100 or the test device 200, or in one of the remote and/or distributed databases and/or servers. Preferably, one or more of the algorithms 214 generate the test results 412 and/or the presentation data 400 for presentation from the display element 112 in the form of one or more visually presentable textual data, graphical data, or colored indicator light data. Data compilation and report design is performed, preferably using the presentation data 400.

Preferably thereafter, in the presentation step 510, 610, the user may preferably be provided with access to the test results 412, preferably via the display element 112 of the electronic device 100. That is, the presentation data 400 (e.g., the test results 412 and treatment and follow-up suggestion data) are presented to the user using the presentation element 110 of the electronic device 100. Preferably, in the presentation step 510, 610, the presentation data 400 are presented from the display element 112 of the presentation element 110.

The electronic device processor 108 may preferably be operative, in the presentation step 510, 610, to display combined test information, including the test results 412 together with time and date data 402 and geo-localization data 404 for the test, and with the patient ID data 410 and other information inputted in the data input step 516, 616 from the electronic device screen 112.

Thereafter, in a test strip release step 532, the electronic device processor 108 may be operative to display a "Release Test Strip" message as a pop-up window on the electronic device screen 112, and/or to eject the test cartridge 20 from the test device 200.

In the encryption step, the algorithms 214 operatively loaded onto the electronic device processor 108 may be automatically operative to encrypt the test information into encrypted information, using methods described elsewhere herein, so as to make it HL7 and/or ASTN compliant. The encryption step may, according to some or all of the preferred embodiments of the invention, also be performed prior to storage of any data onboard the electronic device 100. In this manner, no patient ID data 410 will reside, in an un-encrypted form, in the memory of the electronic device 100.

According to some alternate embodiments of the invention, upon removal of the test strip, the user may be automatically presented with a remote transmission query 534 which affords a wireless transmission option (e.g., a "Transmit Data?" query and the option to select "Yes" or "No") on the electronic device screen 112. If "No" is selected in response to remote transmission query 534, the electronic device processor 108 may preferably skip the networking step, i.e., without wireless transmission of any data. Preferably, however, the user is not presented with such an option and wireless transmission to a remote and/or distributed database and/or server takes place automatically (in accordance with the networking step 536, 636).

In the networking step 536, 636, the electronic device 100 may send the encrypted data 426 to a remote and/or distributed database and/or server. According to some preferred embodiments of the invention, the remote and/or distributed database and/or server may preferably (but need not necessarily) include one or more remote laboratory and/or hospital information systems.

After that, according to some embodiments of the invention, prior to the encryption and networking steps 536, the electronic device 100 may preferably provide an option— e.g. via presentation of a remote transmission query 534 on the display element 112—to transfer onboard data to the remote and/or distributed databases and/or servers. Though not shown in the drawings, according to some alternate embodiments of the invention, the user may also be presented with an option to keep the data inside the electronic device 100, and/or to keep the data inside the test device 200.

In the encryption and networking steps 536, 636, the electronic device 100 is preferably used to automatically transmit the test data, the test results 412, the presentation data 400, and/or the encrypted data 426 for recordal in one or more of the remote and/or distributed databases and/or servers (e.g., laboratory and/or hospital information systems).

Thereafter, the user is preferably automatically presented with an option to obtain information concerning recommended treatment (e.g., by way of a treatment information query 540 and the option to select "Yes" or "No") on the electronic device screen 112. If "Yes" is selected in response to the treatment information query 540, treatment information may be provided via database(s) internal and/or external to the integrated device, and presented from the presentation element 110 of the electronic device 100. On the other hand, if "No" is selected in response to the treatment information query 540, the electronic device processor 108 may proceed directly to a print test results query 544, i.e., without providing any treatment information.

The print test results query 544 may preferably be automatically presented to the user and affords an option to print or otherwise output the test information in a print test results step 546.

Thereafter, in a test completion step 548, 648, the electronic device processor 108 finishes processing of the test data detected from the test cartridge 20, freeing processing capability to process the test data from another test cartridge 20

It may be appreciated that, once the algorithms 214 are uploaded to the electronic device 100, the electronic device 100 performs key functions which effectively control all, or at least a substantial portion, of the process described herein.

It may be understood the test device 200 may preferably function as a universal rapid diagnostic test device. That is, any prior art test which makes use of a known assay and/or reagents may be performed using the test device 200 according to the present invention. Moreover, the test cartridge identification data 416 encoded by the barcode (or other test cartridge identification element) 24 may enable the electronic device processor 108, after upload of the algorithms 214, to ascertain which prior art rapid diagnostic test, assay and/or reagents is to be performed and the appropriate calibration and assay time counting which is to be associated therewith.

Figure 6:
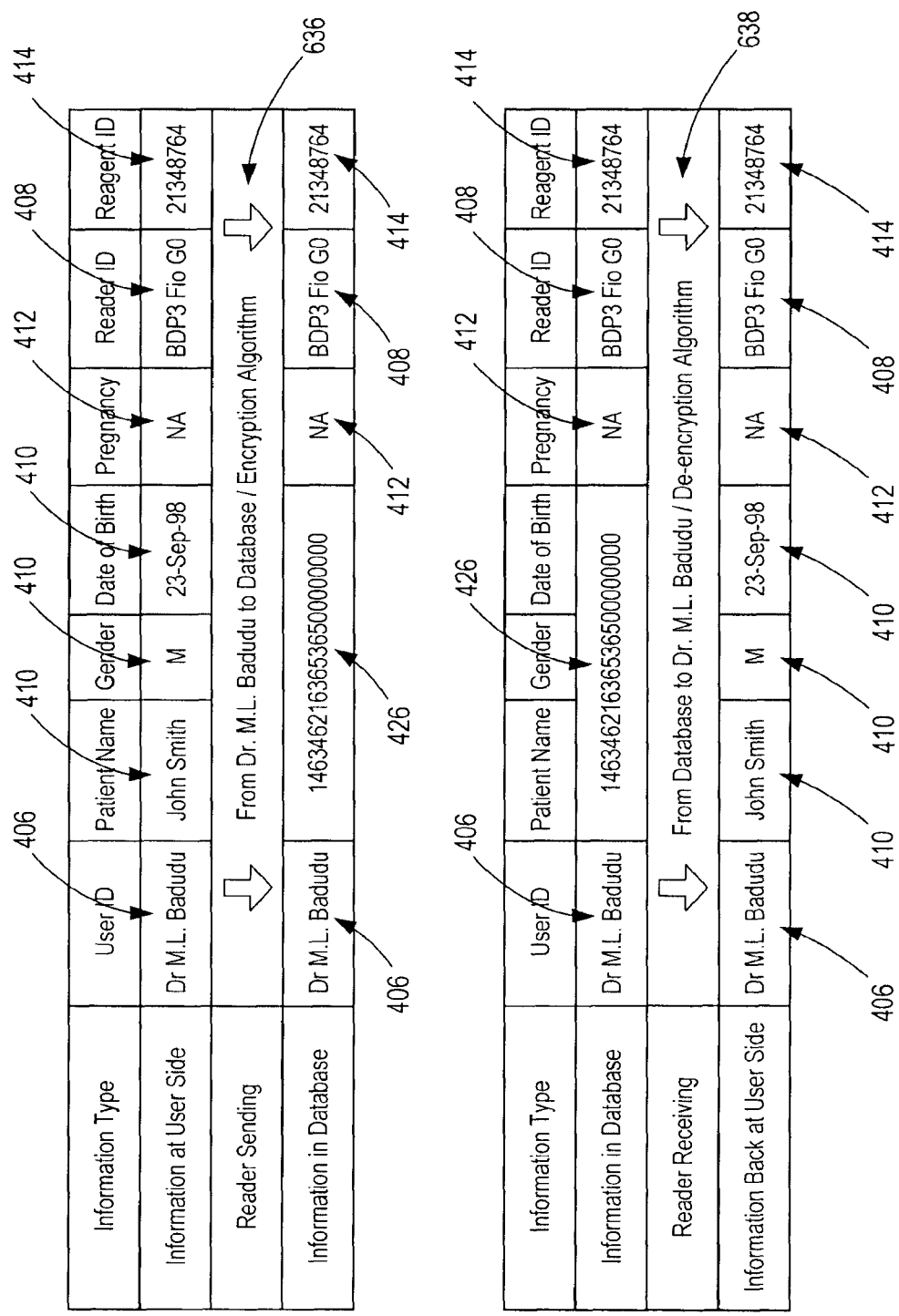
FIG. 6 is a graphic representation of data processed by the electronic device of FIG. 1A or 1B according to the invention.
Figure 7:
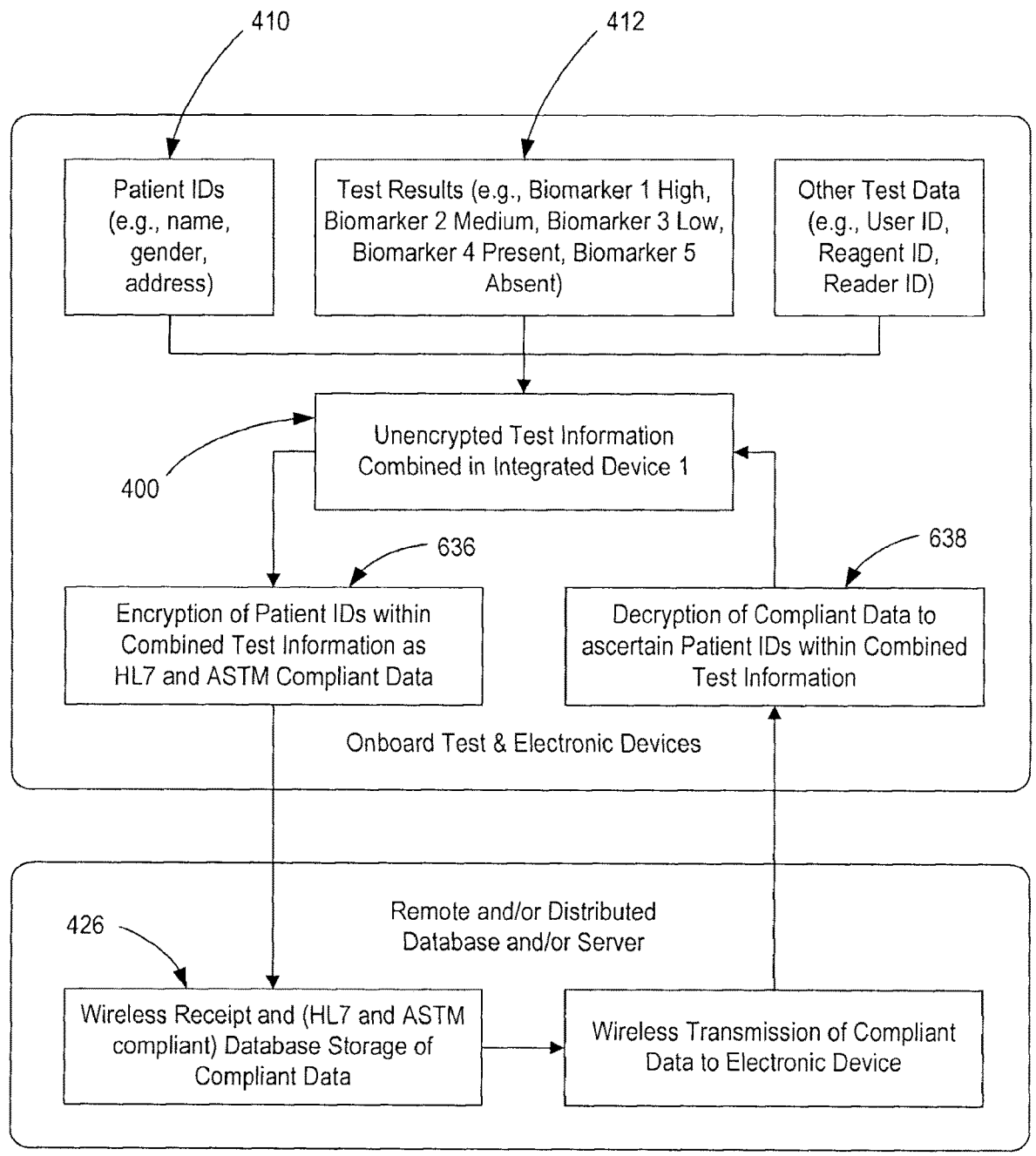
FIG. 7 is a schematic diagram of data management according to the invention.

Preferably, the data collected according to the present invention may be managed largely via the algorithms 214 which are operatively loaded onto the electronic device 100. According to the present invention, and as best seen in FIGS. 6 and 7, sensitive patient ID information 410 is advantageously encrypted prior to transmission of any collected data by the user to the remote and/or distributed database. Also, FIGS. 6 and 7 are illustrative of the advantageous de-encryption of the user's and/or the device's previously collected data (e.g., whether maintained by the user or otherwise) which may preferably be performed, according to the present invention, when the encrypted patient ID information 410 is received back—i.e., received by the same user and/or device that had previously collected the patient ID information 410—from a local, remote and/or distributed database.

The decryption (alternately herein "de-encryption")—which may be performed as part of a receiving and decryption step 638 according to the present invention—may be portably associated with the test device 200, the electronic device 100, and/or the user. According to some preferred embodiments of the invention, each user may be provided with their own de-encryption tool associated with their user ID information 406, so that they can still access and de-encrypt data which they may have previously collected using a different test device 200 and/or electronic device 100.

Preferably, according to the present invention, an encrypted and/or anonymized database may be created which may enable certain health providers to download and de-encrypt the data relating to their specific patients. Preferably, such a database may permit sale of anonymized data while still favorably improving the ability of such health providers to provide a patient-specific emergency medical response (EMR).

The encrypted and/or anonymized database may also preferably enable pharmaceutical and other companies to indirectly request patient enrollment in clinical trials, by requests sent via patients' healthcare providers. This mechanism may afford increased security over patient data, and/or improved peace of mind amongst patients and healthcare providers—not giving any cause for worry over companies having direct access to patient information without permission.

It may be appreciated from the foregoing that, according to the present invention, the test device 200 is a medical device and the electronic device 100 is preferably an electronic network and/or communication device. As such, the test device 200 may require regulatory approval by a governmental body or other organization prior to deployment in the field. Perhaps notably, the electronic device 100 need not obtain such approval. According to some preferred embodiments of the present invention, the electronic device 100 may be responsible for providing one or more of the following: display of diagnostic data, management of patient IDs, diagnostic profiling, HL7 and/or ASTM compliant processes, transfer of data to the remote database, communication with the test device processor 216 and the remote database, data storage, assay time countdown and display, treatment information, and/or various other interfaces. According to some preferred embodiments of the present invention, the test device 200 on the other hand may be responsible for providing one or more of the following: raw data acquisition, self-checking functionality, assay cut-off values, test result algorithms, assay calibration curves, communication with and data transfer to the electronic device processor 108, and/or a printer. It may be important to note that the above-listed functionalities of the electronic device 100 and test device 200, respectively, are preferred functionalities and need not necessarily be so. It should be appreciated that another potential advantageous utility afforded by the present invention is that it enables an ordinary electronic device 100 to be used without requiring its special regulatory approval. Additionally, the speed and costs associated with bringing to market new test devices 200 according to the present invention may be advantageously reduced.

It may be appreciated by persons having ordinary skill in the art that, with utilization of the test device 200 and methods 500, 600 (together with the functionalities specified herein for the electronic device 100 operatively loaded with the algorithms 214) according to the present invention, it may preferably be possible to greatly improve upon the limited functionality which may have been afforded by prior test devices.

The test device 200 and methods 500, 600 (together with the functionalities specified herein for the electronic device 100 operatively loaded with the algorithms 214) according to the present invention are unlike anything in the prior art—in a number of important ways (as may be appreciated by persons having ordinary skill in the art in view of the disclosures elsewhere herein). For example, the test device 200 and the electronic device 100 (operatively loaded with the algorithms 214 according to the present invention) together provide a compact envelope which houses powerful patient data management capabilities, in ready and facile combination with network communication and/or location positioning system capabilities.

When all of the foregoing functionalities are combined with the relatively low total cost associated with the test device 200, it may additionally be appreciated that same may be affordable for use in developing countries.

This concludes the description of presently preferred embodiments of the invention. The foregoing description has been presented for the purpose of illustration and is not intended to be exhaustive or to limit the invention to the precise form disclosed. Other modifications, variations and alterations are possible in light of the above teaching and will be apparent to those skilled in the art, and may be used in the design and manufacture of other embodiments according to the present invention without departing from the spirit and scope of the invention. It is intended the scope of the invention be limited not by this description but only by the claims forming a part of this application and/or any patent issuing herefrom.

What is claimed is:

1. A method of testing a biological and/or environmental sample for use with one or more reagents carried by a universal test cartridge in a rapid diagnostic test, an ordinary networking electronic device that does not require regulatory approval as a medical device, and a handheld diagnostic test device, the method comprising:

(a) a connecting step of connecting a universally connectable test device connection element of the test device with a universally connectable electronic device connection element of the networking electronic device;

(b) an uploading step, after the connecting step, of electronically transmitting one or more algorithms to process test data using the networking electronic device that are electronically stored in an onboard memory of the test device to the networking electronic device, via the test device connection element and the electronic device connection element;

(c) a presentation step, after the uploading step, of using the one or more algorithms to enable an electronic device processor onboard the networking electronic device to present presentation data from an electronic device presentation element onboard the networking electronic device to a user;

(d) a cartridge inserting step, after the connecting step and the uploading step, of inserting the test cartridge into a port in the test device, with the test cartridge serving as a substrate for reaction of the sample with the reagents;

(e) a waiting step of using the one or more algorithms to enable the electronic device processor to await elapse of a pre-determined time following reaction of the sample with the reagents;

(f) a sensing step, after the waiting step and the cartridge inserting step, of using the one or more algorithms to enable the electronic device processor to control the test device and instruct one or more sensors to detect test data from the sample;

(g) an electronic device processing step, after the sensing step, of using the one or more algorithms to enable the electronic device processor to generate, based on the test data, at least a portion of the presentation data presented to the user; and (h) a transmission step, after the electronic device processing step, wherein the networking electronic device transmits, without the patient identification data and fully compliant with all applicable interface standards for exchanging and transferring health data, at least a portion of the presentation data, the test data, and the encrypted data for recordal in one or more remote and/or distributed databases;

wherein all or substantially all processing and management of the test data, and all processing and management of the presentation data, is performed remotely of the test device.

2. A method according to claim 1, wherein in the connecting step, the test device connection element is connected with the electronic device connection element in selectively disconnectable relation.

3. A method according to claim 1, wherein during the waiting step, the algorithms enable the electronic device processor to generate time counting data, with the time counting data forming at least a portion of the presentation data presented to the user.

4. A method according to claim 1, wherein before the electronic device processing step, the test data is electronically transmitted from the sensors to the electronic device via the test device connection element and the electronic device connection element; and wherein in the electronic device processing step, the algorithms enable the electronic device processor to generate test results based on the test data, with the test results forming at least part of the presentation data for presentation to the user.

5. A method according to claim 1, further comprising a test device processing step, before the electronic device processing step, of using a test device processor onboard the test device to electronically receive the test data from the sensors and to generate test results based on the test data; wherein before the electronic device processing step, the test results are electronically transmitted from the test device connection element to the electronic device via the electronic device connection element; and wherein in the electronic device processing step, the algorithms enable the electronic device processor to generate the presentation data based at least in part on the test results.

6. A method according to claim 4, wherein in the electronic device processing step, the algorithms enable the electronic device processor to generate treatment and follow-up suggestion data for presentation to the user as at least part of the presentation data, with the treatment and follow-up suggestion data being based at least in part on the test results.

7. A method according to claim 1, wherein in the connecting step, the test device connection element is physically connected with the electronic device connection element in mating relation.

8. A method according to claim 1, further comprising a cartridge identification step, before the electronic device processing step, of using at least one of the sensors to operatively detect test cartridge identification data from a test cartridge identification element onboard the test cartridge, and using the test cartridge identification data to identify the rapid diagnostic test, the reagents, and/or associated quality assurance information.

9. A method according to claim 8, wherein in the cartridge identification step, a bar code element and/or a radio-frequency identification (RFID) element is used as the test cartridge identification element.

10. A method according to claim 1, further comprising a maintenance step, after the uploading step, of using the algorithms to enable the electronic device processor to instruct the test device to initiate a self-check, calibration and/or maintenance routine.

11. A method according to claim 1, further comprising a data input step, after the uploading step, of using the algorithms to enable the electronic device processor to electronically receive, via a data input device onboard the electronic device, user and/or patient identification data associated with the rapid diagnostic test; and wherein in the electronic device processing step, the algorithms enable the electronic device processor to generate the presentation data based in part on the user and/or patient identification data for presentation to the user.

12. A method according to claim 11, wherein in the data input step, a keypad is used as the data input device.

13. A method according to claim 11, wherein in the connecting step, the electronic device is a networking electronic device; with the method further comprising an encryption step, after the data input step, of using the algorithms to enable the electronic device processor to encrypt the patient identification data as encrypted data; and a networking step, after the electronic device processing step and the encryption step, of using the algorithms to enable the electronic device to transmit, without the patient identification data, at least a portion of the presentation data, the test data, and the encrypted data for recordal in one or more remote and/or distributed databases; wherein in the networking step, the transmission of the presentation data, the test data, and the encrypted data by the electronic device and the encryption of the patient identification data is fully compliant with all applicable interface standards for exchanging and transferring health data.

14. A method according to claim 11, wherein in the networking step, the applicable interface standards for exchanging and transferring health data comprise the HL7 standard and/or the ASTM standard.

15. A method according to claim 1, wherein in the connecting step, the electronic device is a networking electronic device; with the method further comprising a networking step, after the electronic device processing step, of using the algorithms to enable the electronic device to transmit at least a portion of the presentation data and/or the test data for recordal in one or more remote and/or distributed databases.

16. A method according to claim 13, further comprising a geo-localization step, before the networking step, of using the algorithms to enable the electronic device processor to use a geo-localization element onboard the electronic device to obtain geo-localization data for the rapid diagnostic test;

and wherein in the networking step, the algorithms enable the networking electronic device to transmit the geo-localization data for recordal in the remote and/or distributed databases.

17. A method according to claim 1, wherein in the sensing step, a light source element onboard the test device illuminates the sample, and at least one of the sensors comprises a photodiode element, with the test data comprising a test image.

18. A method according to claim 17, wherein in the sensing step, the photodiode element comprises a charge coupled device (CCD) element.

19. A method according to claim 17, wherein in the sensing step, the light source element comprises a laser, a light emitting diode (LED), an optical fiber light source element, a tungsten lamp, a mercury lamp, and/or a xenon lamp.

20. A method according to claim 1, further comprising a storage step, after the sensing step, of using the algorithms to enable the electronic device processor to store the presentation data and/or the test data in an electronic device memory onboard the electronic device.

21. A method according to claim 1, wherein in the presentation step, the presentation element is a display element, and the algorithms enable the electronic device processor to generate the presentation data for presentation from the display element in the form of one or more visually presentable (a) textual data, (b) graphical data, and/or (c) colored indicator light data.

22. A method according to claim 1, further comprising a powering step, before the uploading step, of using a test device battery onboard the test device to power the test device.

23. A method according to claim 1, further comprising a powering step, before the uploading step, of using an electronic device battery onboard the electronic device to transmit power to the test connection element of the test device, via the electronic connection element.

24. A method according to claim 1, wherein in the connecting step, one or more of following is used as the electronic device: (a) a cellular telephone; (b) a mobile communications device; (c) a personal digital assistant; (d) a desktop computer; (e) a laptop computer; (f) a navigation device; (g) a digital audio player; (h) a camera; (i) a gaming device; (j) a television; and/or (k) a radio.

* * * * *